(12) United States Patent
Powell et al.

(10) Patent No.: US 7,943,664 B2
(45) Date of Patent: May 17, 2011

(54) PHOSPHATE BINDING MATERIALS AND THEIR USES

(75) Inventors: Jonathan Joseph Powell, Cambridge (GB); Nuno Jorge Rodrigues Faria, Bedford (GB)

(73) Assignee: Medical Research Council, London (GB)

( * ) Notice: Subject to any disclaimer, the term of this patent is extended or adjusted under 35 U.S.C. 154(b) by 0 days.

(21) Appl. No.: 12/536,014

(22) Filed: Aug. 5, 2009

(65) Prior Publication Data

US 2010/0032374 A1 Feb. 11, 2010

Related U.S. Application Data

(60) Provisional application No. 61/086,244, filed on Aug. 5, 2008.

(30) Foreign Application Priority Data

Aug. 5, 2008 (GB) .................................. 0814326.5

(51) Int. Cl.
*A61K 31/295* (2006.01)
*A61K 31/19* (2006.01)
(52) U.S. Cl. .......................... 514/502; 514/557; 514/574
(58) Field of Classification Search .................. 514/502, 514/557, 574
See application file for complete search history.

(56) References Cited

U.S. PATENT DOCUMENTS

| | | | | |
|---|---|---|---|---|
| 5,514,281 A | * | 5/1996 | Boos et al. | |
| 6,174,442 B1 | * | 1/2001 | Geisser et al. | |
| 6,903,235 B2 | * | 6/2005 | Hsiao et al. | |
| 2008/0188555 A1 | | 8/2008 | Powell et al. | |

FOREIGN PATENT DOCUMENTS

| | | | |
|---|---|---|---|
| WO | 2004074444 A2 | | 9/2004 |
| WO | 2007088343 A2 | * | 8/2007 |
| WO | 2008071747 A1 | | 6/2008 |
| WO | 2008096130 A1 | | 8/2008 |
| WO | 2009062993 A1 | | 5/2009 |

OTHER PUBLICATIONS

V. Autissier et al.. "Relative in vitro Efficacy of the Phosphate Binders Lanthanum Carbonate and Sevelamer Hydrochloride", J. Pharm. Sci., 96: 2818-2827 (2007).
V.A. Drits et al., "Structural Model for Ferrihydrite", Clay Minerals 28: 185-207 (1993).
D. Janney et al., "Transmission Electron Microscopy of Synthetic 2- and 6-Line Ferrihydrite", Clays and Clay Minerals, 48(1): 111-119 (2000).
D. Mavrocordatos et al., "Quantitative characterization of biotic iron oxides by analytical electron microscopy", American Mineralogist, 87: 940-946 (2002).
Y. Pan et al., "Electron beam damage studies of synthetic 6-line ferrihydrite and ferritin molecule cores within a human liver biopsy", Micron, 37: 403-411 (2006).
F. Marc Michel et al., "The Structure of Ferrihydrite, a Nanocrystalline Material", Science, 316: 1726-1729 (2007).
Y. Maeda et al., "Correlation between Detrapped Valence States and Molecular Packing of Mixed-Valence Dinuclear Iron (II,III) Complexes of a Septadentate Polypyridine Ligand", Chemistry Letters, 1: 65-66 (1995).
R.B. Lanjewar et al., "Quadrupole Hyperfine Interaction in Iron(III) Dicarboxylic Acid Complexes", J. Radioanalytical and Nuclear Chemistry, 125(1): 75-84 (1988).
Z. Smekal et al., "Binuclear iron(III)-iron(III) complexes with the tetradentate Schiff base, N,N'-bis(salicylidene) ethylenediamine and dicarboxylic acids or dithiooxamide as bridging ligands", Transition Met. Chem., 21: 49-51 (1996).
C.L. Sharma et al., Mossbauer Studies on Some Penta Coordinated Mixed Ligand Complexes of Iron(III), Chemica Scripta, 18(3): 133-134 (1981).
M. Bobtelsky et al., "The Structure and Behavior of Ferric Tartrate and Citrate Complexes in Dilute Solutions", J. Amer. Chem. Soc., 69(10): 2286-2290 (1947).
R.S.J. Harvey et al., "Ferric trimaltol corrects iron deficiency anaemia in patients intolerant of iron", Alimentary Pharm. and Ther., 12(9): 845-848 (1998).
H.C. Heinrich, "Bioavailability of Trivalent Iron in Oral Iron Preparations", Drug Res., 25(3): 420-426 (1975).
P. Geisser et al., Pharmacokinetics of Iron Salts and Ferric Hydroxide-Carbohydrate Complexes, Drug Res., 37: 100-104 (1987).
P. Nielsen et al., "Bioavailability of Iron from Oral Ferric Polymaltose in Humans", Drug. Res., 44(6): 743-748 (1994).

* cited by examiner

*Primary Examiner* — Raymond J Henley, III
(74) *Attorney, Agent, or Firm* — Patrick J. Hagan; Dann, Dorfman, Herrell and Skillman, P.C.

(57) ABSTRACT

Phosphate binding materials and compositions comprising them which are solid ligand-modified poly oxo-hydroxy metal ion materials are disclosed that are based on ferric iron oxo-hydroxides modified with carboxylic acid ligands, or ionized forms thereof. These materials are made and tested in the examples provided in the application to demonstrate that they can bind phosphate in in vitro and in in vivo studies.

35 Claims, 10 Drawing Sheets

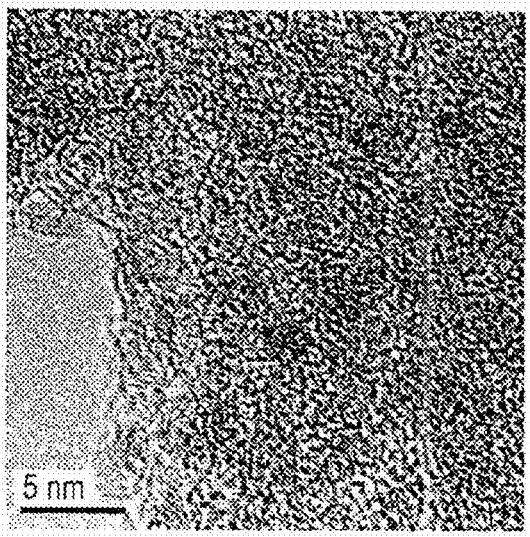
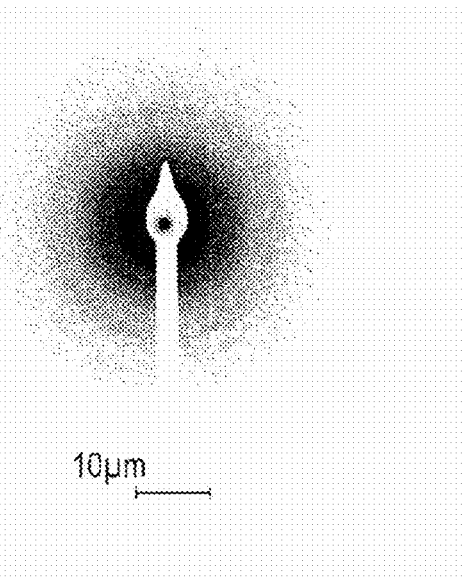
FIG. 10a    FIG. 10b
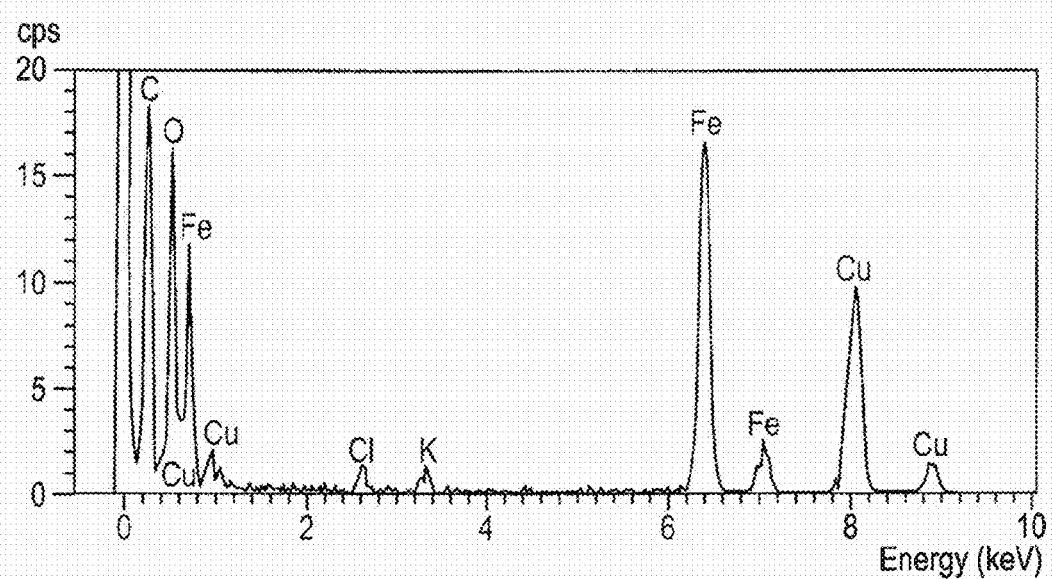
FIG. 10c

PHOSPHATE BINDING MATERIALS AND THEIR USES

CROSS-REFERENCE TO RELATED APPLICATIONS

The present application claims the benefit of U.S. Provisional Patent Application No. 61/086,244, filed Aug. 5, 2008, the entire disclosure of which is incorporated by reference herein.

FIELD OF THE INVENTION

The present invention relates to phosphate binding materials and their uses in the treatment of hyperphosphatemia and for removing phosphate from materials, for in vitro and in vivo applications. More particularly, the present invention relates to phosphate binding materials which are ligand-modified ferric poly oxo-hydroxy materials.

BACKGROUND OF THE INVENTION

Phosphate levels are regulated predominantly by the kidneys and in healthy people phosphate homeostasis is maintained by urinary excretion. Phosphate concentrations in serum can increase dramatically in patients with chronic renal failure and lead to secondary hyperthyroidism and soft tissue calcification. This calcification results in atherosclerosis of the coronary arteries and premature heart disease, which is the major cause of death in end-stage renal disease (ESRD). Dietary phosphate restriction alone is usually insufficient to control hyperphosphatemia in haemodialysis patients and the oral intake of phosphate binders is required to reduce intestinal absorption.

Aluminium and calcium compounds have been widely used to bind dietary phosphate, but there are concerns regarding their long-term safety. The use of aluminium-based phosphate binders results in tissue accumulation of this element and may result in systemic toxicity. The administration of large quantities of calcium-based phosphate binders can result in hypercalcemia and subsequently aggravate tissue calcification.

Sevelamer (polyallylamine hydrochloride), a synthetic polymer commercialised under the name of Renagel, is an anion exchange resin used to bind dietary phosphate. However, the binding action of this resin is not specific to phosphate and large doses have to be administered to control serum phosphate in ESRD patients, which can lead to low patient compliance. Lanthanum carbonate is an approved phosphate binder commercialised under the name of Fosrenol. However, concerns exist about the long-term accumulation and toxicity of lanthanum in tissues.

U.S. Pat. No. 6,903,235 describes the use of ferric citrate, a soluble iron compound, to bind dietary phosphate. However, the long-term use of a soluble iron compound is likely to lead to gastrointestinal side-effects due to the redox activity of free iron in the gut lumen, which may subsequently result in low compliance.

WO 2007/088343 describes a phosphate binder formed from the reaction of aqueous solutions of magnesium sulphate and ferric sulphate in the presence of sodium hydroxide and sodium carbonate, probably leading to an iron magnesium hydroxy carbonate with an hydrotalcitic structure. This phosphate binder is known as "Alpharen", but suffers from the disadvantage that it binds relatively small amounts of phosphate and moreover releases $Mg^{2+}$ in the stomach, leading to frequent side-effects.

The ability to bind phosphate by iron oxo-hydroxides is known in the art. For example, U.S. Pat. No. 6,174,442 describes an adsorbent for phosphate using β-iron hydroxide stabilized by carbohydrates and/or humic acid. However, its binding ability is limited and the manufacturing process is unsuitable for the preparation of large quantities of material. WO 2008/071747 describes an adsorbent for phosphate containing γ-iron oxide-hydroxide stabilized by insoluble and soluble carbohydrates. However, the phosphate binding activity of the materials described therein is limited to very low pH, limiting its effectiveness as a phosphate binder.

In summary, there is no ideal phosphate binder in current use and existing materials have one or many flaws, most commonly toxicity or accumulation, cost, efficacy of phosphate removal, acidosis and/or patient intolerance.

Accordingly, there remains a continuing need in the art to develop further phosphate binders that overcome or ameliorate some of the drawbacks of existing treatments.

SUMMARY OF THE INVENTION

Broadly, the present invention relates to phosphate binding materials and compositions comprising them which are solid ligand-modified poly oxo-hydroxy metal ion materials. The compositions disclosed herein are based on ferric iron oxo-hydroxides modified with carboxylic acid ligands, or ionised forms thereof, such as adipate. These materials are made and tested in the examples provided in the application to demonstrate that they can bind phosphate in in vitro and in in vivo studies.

Accordingly, in a first aspect, the present invention provides a ferric iron composition for use in a method of treating hyperphosphatemia, wherein the ferric iron composition is a solid ligand-modified poly oxo-hydroxy metal ion material represented by the formula $(M_xL_y(OH)_n)$, wherein M represents one or more metal ions that comprise $Fe^{3+}$ ions, L represents one or more ligands that comprise a carboxylic acid ligand, or an ionised form thereof, and OH represents oxo or hydroxy groups and wherein the material has a polymeric structure in which the ligands L are substantially randomly substituted for the oxo or hydroxy groups. It is preferred that the solid ligand-modified poly oxo-hydroxy metal ion material has one or more reproducible physico-chemical properties, for example dissolution profile and/or phosphate binding characteristics. As discussed further below, the ferric iron materials of the present invention preferably have structures which are consistent with ligand-modified ferrihydrite. It is also preferred that the ferric iron materials of the present invention have demonstrable M-L bonding using physical analysis, such as infrared spectroscopy.

In a further aspect, the present invention provides the use of a ferric iron composition of the present invention for the preparation of a medicament for the treatment of hyperphosphatemia.

In a further aspect, the present invention provides a method of treating hyperphosphatemia, the method comprising administering to a patient in need of treatment a therapeutically effective amount of a ferric iron composition of the present invention.

In a further aspect, the present invention provides a method for removing phosphate from a medium, the method comprising (a) contacting a medium containing phosphate with a ferric iron composition of the present invention under conditions in which the phosphate is capable of binding to the ferric iron composition and (b) separating the bound phosphate from the composition. This method may be used in vitro or in vivo. Accordingly, the materials described herein are capable of selectively removing phosphate from solutions or suspensions containing this anion. The removal might take place in vivo, for example where the materials described herein are capable of removing phosphate from the liquid or sludge-like contents of the gastrointestinal tract following oral administration. However, the materials of the present invention may find other applications, for example where the materials are capable of removing phosphate from food-stuffs prior to consumption, or are capable of selectively removing phosphate from dialysis fluids, plasma and/or whole blood. One particular application of the phosphate binders of the present invention is in dialysis where they may be used for the extracorporeal removal of phosphate from dialysis fluids during haemodialysis processes. In this aspect, the present invention provides compositions such as a food-stuff or dialysis fluid that comprise a phosphate binding material of the present invention.

Accordingly, the present invention provides a method to treat high plasma phosphorus levels, hyperphosphatemia arising from any level of renal insufficiency, acute renal failure, chronic renal failure, and/or end-stage renal disease, including conditions that require haemodialysis. The clinical management of these conditions using the present invention may help to ameliorate complications associated with these conditions, such as secondary hyperthyroidism, soft tissue calcification, osteodystrophy, hypercalcaemia, hyperparathyroidism reduction, cardiovascular morbidity or mortality, renal osteodystrophy and/or calciphylaxis.

In one aspect, the present invention provides a process comprising the steps of producing a ferric iron material and testing it to determine whether, or to what extent it is capable of binding phosphate. By way of example, the process may comprise:
(a) mixing the solution comprising $Fe^{3+}$ and carboxylic acid ligand (e.g. adipic acid), and any additional ligands or other components, in a reaction medium at a first pH(A) at which the components are soluble;
(b) changing the pH(A) to a second pH(B) to cause a solid precipitate or a colloid of the ligand-modified poly oxo-hydroxy metal ion material to be formed;
(c) separating, and optionally drying and/or formulating, the solid ligand-modified poly oxo-hydroxy metal ion material produced in step (b).

Embodiments of the present invention will now be described by way of example and not limitation with reference to the accompanying figures and examples.

BRIEF DESCRIPTION OF THE FIGURES

FIG. 10: a) The primary particles (crystallites) of FeOH Ad100 show up as 2-3 nm, dark, mottled particles in a high resolution TEM image of the powder, and appear less crystalline than unmodified ferrihydrite (not shown). b) The underlying ferrihydrite-like structure is apparent from electron diffraction with plane spacings at 2.5 and 1.5 Å. c) EDX spectrum shows major elements of FeOH Ad100 to be C, O and Fe with minor contributions from Cl (~1.4 at. %), K (~1.2 at. %), and possibly Na. The Cu signal is due to the support grid.

DETAILED DESCRIPTION

The Metal Ion (M)

Figure 1:
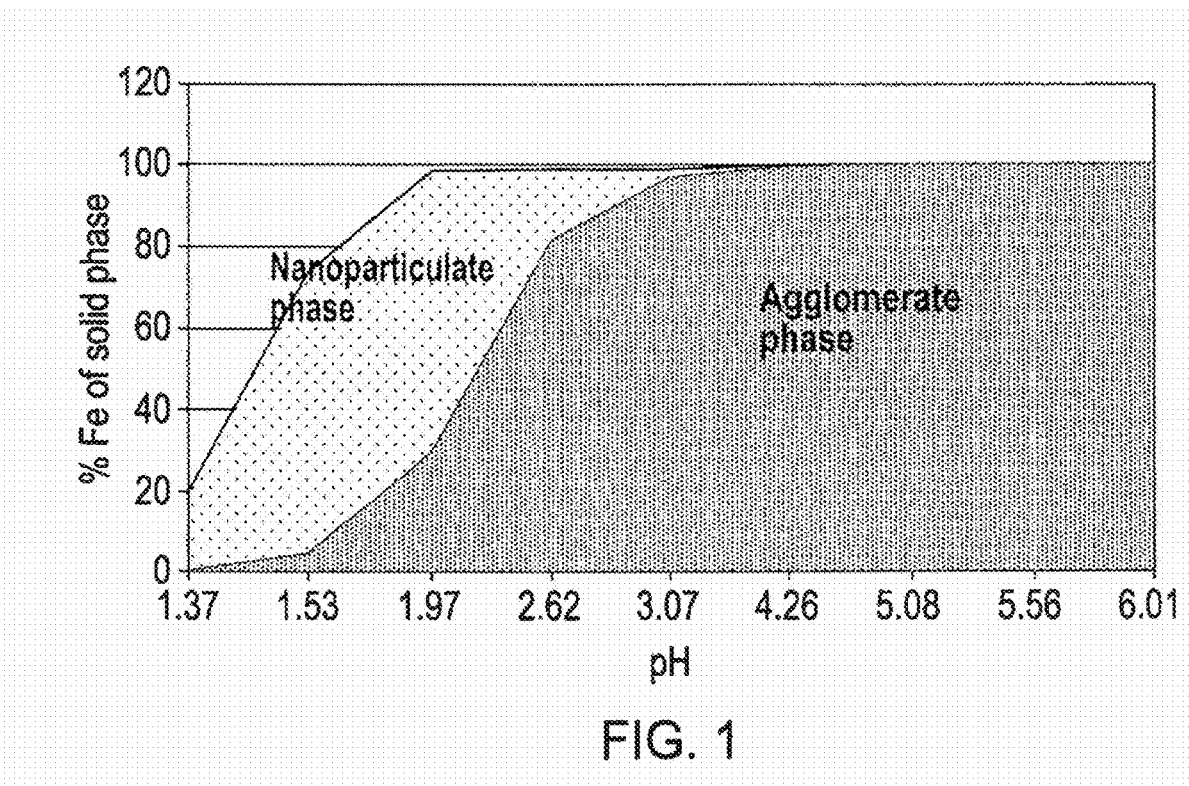
FIG. 1: Evolution of FeOH Ad100 precipitation with increasing pH, expressed as the percentage of total iron in the starting solution. A fully precipitated and agglomerated phase is achieved at pH 4.5.

The production and characterisation of solid ligand-modified poly oxo-hydroxy metal ion materials is disclosed in our earlier application PCT/GB2008/000408 (WO 2008/096130) filed on 6 Feb. 2008. These materials, including those that comprise ferric iron ($Fe^{3+}$), that are used to form the phosphate binding materials disclosed herein, may be represented by the formula ($M_xL_y(OH)_n$), where M represents one or more metal ions. Normally, the metal ion will originally be present in the form of a salt that in the preparation of the materials may be dissolved and then induced to form poly oxo-hydroxy co-complexes with ligand (L). In some embodiments, the metal ions substantially comprise ferric iron ($Fe^{3+}$), as opposed to a combination of metal ions being present, or the metal ions including iron in other oxidation states, such as $Fe^{2+}$. Preferably, some of the ligand used is integrated into the solid phase through formal M-L bonding, i.e. not all of the ligand (L) is simply trapped or adsorbed in the bulk material. The bonding of the metal ion in the materials can be determined using physical analytical techniques such as infrared spectroscopy where the spectra will have peaks characteristic of the bonds between the metal ion and the ligand (L), as well as peaks characteristic of other bonds present in the material such as M-O, O—H and bonds in the ligand species (L). The phosphate binders disclosed herein use ferric iron ($Fe^{3+}$) to provide compositions that are biologically compatible under the conditions for which the materials are used, for example to ameliorate some of the drawbacks of the prior art phosphate binding compositions which tend to be systemically toxic or have binding properties that are not specific to phosphate.

By way of background, it is well known in the art that iron oxides, hydroxides and oxo-hydroxides are composed of Fe together with O and/or OH and are collectively referred to in this patent and known in the art as iron oxo-hydroxides. Different iron oxo-hydroxides possess different structures and elemental compositions which in turn determine their physicochemical properties (see Cornell & Schwertmann, The Iron Oxides Structure, Properties, Reactions, Occurrence and Uses. 2nd ed, 1996, VCH Publishers, New York). For example, Akageneite (β- or beta-iron oxo-hydroxide) contains chloride or fluoride in its intrinsic structure and forms spindle or rod-shaped crystals. Maghemite (γ- or gamma-iron oxide) contains cation deficient sites and typically shows ferromagnetic properties. This material tends to produce cubic crystals. Ferrihydrite is a further example of an iron oxo-hydroxide material that shows a lower level of structural order than the akageneite and maghemite and produces spherical crystals. The experiments disclosed herein demonstrate that the phosphate binders disclosed herein, such as FeOH Ad100, preferably have a ferrihydrite-like structure and preferably a structure consistent with 2-line ferrihydrite. By way of example, the skilled person can assess whether a material has a 2-line ferrihydrite structure using a diffraction technique, preferably using electron diffraction, a technique in which electrons that bombard a sample in an electron microscope are scattered in a fashion that reflects the internal order of the primary particle of the material, and produces a spectrum that is similar to that of 2-line ferrihydrite, as opposed to other forms of iron oxo-hydroxide. Alternatively or additionally, the size and morphology of particles of the phosphate binders of the present invention, when viewed with electron microscopy, is similar to that of 2-line ferrihydrite. However, it should be noted that although from electron studies the size, morphology and atomic ordering of the primary particle appears similar to that of 2-line ferrihydrite, the material is not 2-line ferrihydrite, rather a ligand modified form of it. This is apparent firstly from in vitro phosphate binding studies where the materials claimed herein consistently and significantly show an enhancement of phosphate binding ability in relation to unmodified 2-line ferrihydrite. Secondly, dissolution studies show that at an acidic pH, typically at or below pH 1.2, the materials of the present invention have rapid dissolution, a physico-chemical parameter that is not observed with 2-line ferrihydrite.

Similarly, it is preferred that the materials of the present invention have a significantly higher phosphate binding capacity than 2-line ferrihydrite at a range of pHs that may be experienced post prandially in the gastrointestinal tract, for example from pH 3-7. An exemplary assay for determining phosphate binding is reported in the example 2.1 in which equal masses of ferrihydrite (e.g. 53.6 mg), or indeed any other binder used as a comparison, and a phosphate binder of the present invention were assayed to determine the percentage of phosphate they are capable of binding under physiological conditions. In general, the mass of the materials used in the assay may be between 10 mg and 80 mg inclusive in a 20 mL assay. These results show that ferrihydrite binds about 30% of phosphate from 10 mM phosphate solution. In contrast, it is preferred that the phosphate binders of the present invention bind at least 50% of the phosphate, more preferably at least 60%, more preferably at least 70%, and most preferably 80% to 85% or more of the phosphate, illustrating the significant improvements to the properties of the phosphate binders of the present invention as compared to unmodified ferrihydrite.

Infrared analysis shows that unlike with 2-line ferrihydrite the material claimed herein shows bonding consistent with the presence of the added ligand, namely adipate in this particular example.

In summary, the structure of the phosphate binding materials of the present invention is preferably based upon 2-line ferrihydrite, but has been chemically modified in such a way that it has significantly different and novel properties. Accordingly, the materials of the present invention may be described as having structures that are consistent with 2-line ferrihydrite, as determined using TEM imaging and/or electron diffraction (see the examples).

Moreover, by way of comparison with the ferric iron compositions disclosed herein, the presence of formal bonding is one aspect that helps to distinguish the materials of the present invention from other products such as "iron polymaltose" (Maltofer) in which particulate crystalline β-iron oxohydroxide (akageneite) is surrounded by a sugar shell formed from maltose and thus is simply a mixture of iron oxo-hydroxide and sugar at the nano-level (Heinrich (1975); Geisser and Müller (1987); Nielsen et al (1994; U.S. Pat. No. 3,076,798); US20060205691). In addition, the materials of the present invention are metal poly oxo-hydroxy species modified by non-stoichiometric ligand incorporation and should therefore not be confused with the numerous metal-ligand complexes that are well reported in the art (e.g., see WO 2003/092674, WO 2006/037449). Although generally soluble, such complexes can be precipitated from solution at the point of supersaturation, for example ferric trimaltol, Harvey et al. (1998), WO 2003/097627; ferric citrate, WO 2004/074444 and ferric tartrate, Bobtelsky and Jordan (1947) and, on occasions, may even involve stoichiometric binding of hydroxyl groups (for example, ferric hydroxide saccharide, U.S. Pat. No. 3,821,192). The use of hydroxyl groups to balance the charge and geometry of metal-ligand complexes is, of course, well reported in the art (e.g. iron-hydroxymalate, WO 2004/050031) and unrelated to the solid ligand-modified poly oxo-hydroxy metal ion materials reported herein.

Similarly, WO 2008/071747 describes an adsorbent for phosphate containing gamma-iron oxide-hydroxide (maghemite) stabilized by an insoluble and soluble carbohydrates. The production of the material described therein requires the presence of an insoluble carbohydrate, such as starch, which only acts as a physical support for material and does not significantly interact with the iron oxo-hydroxide. The production of the material described therein may also include an optional addition of a soluble carbohydrate, such as sucrose, in the final stages of production. The sole purpose of addition of the soluble carbohydrate described therein is to prevent phase changes due to ageing of the material. In contrast, the ferric iron compositions of the present invention preferably have 2-line ferrihydrite-like structure and do not employ an insoluble carbohydrate as a support material and/or do not modify the properties of the starting material using a soluble carbohydrate.

Without modification, the primary particles of the materials used herein have metal oxide cores and metal hydroxide surfaces and within different disciplines may be referred to as metal oxides or metal hydroxides. The use of the term 'oxohydroxy' or 'oxo-hydroxide' is intended to recognise these facts without any reference to proportions of oxo or hydroxy groups. Hydroxy-oxide could equally be used therefore. As described above, the materials of the present invention are altered at the level of the primary particle of the metal oxohydroxide with at least some of the ligand L being introduced into the structure of the primary particle, i.e. leading to doping or contamination of the primary particle by the ligand L. This may be contrasted with the formation of nano-mixtures of metal oxo-hydroxides and an organic molecule, such as iron saccharidic complexes, in which the structure of the primary particles is not so altered.

The primary particles of the ligand-modified poly oxohydroxy metal ion materials described herein are produced by a process referred to as precipitation. The use of the term precipitation often refers to the formation of aggregates of materials that do separate from solution by sedimentation or centrifugation. Here, the term "precipitation" is intended to describe the formation of all solid phase material, including aggregates as described above and solid materials that do not aggregate but remain as non-soluble moieties in suspension, whether or not they be particulate or nanoparticulate (colloidal or sub-colloidal). These latter solid materials may also be referred to as aquated particulate solids.

In the present invention, reference may be made to the modified metal oxo-hydroxides having polymeric structures that generally form above the critical precipitation pH. As used herein, this should not be taken as indicating that the structures of the materials are polymeric in the strict sense of having a regular repeating monomer unit because, as has been stated, ligand incorporation is, except by co-incidence, non-stoichiometric. The ligand species is introduced into the solid phase structure by substituting for oxo or hydroxy groups leading to a change in solid phase order. In some cases, for example the production of the ferric iron materials exemplified herein, the ligand species L may be introduced into the solid phase structure by the substitution of oxo or hydroxy groups by ligand molecules in a manner that decreases overall order in the solid phase material. While this still produces solid ligand modified poly oxo-hydroxy metal ion materials that in the gross form have one or more reproducible physicochemical properties, the materials have a more amorphous nature compared, for example, to the structure of the corresponding metal oxo-hydroxide. The presence of a more disordered or amorphous structure can readily be determined by the skilled person using techniques well known in the art. One exemplary technique is Transmission electron microscopy (TEM). High resolution transmission electron microscopy allows the crystalline pattern of the material to be visually assessed. It can indicate the primary particle size and structure (such as d-spacing), give some information on the distribution between amorphous and crystalline material, and show that the material possesses a structure consistent with a 2-line ferrihydrite-like structure. Using this technique, it is apparent that the chemistry described above increases the amorphous phase of our described materials compared to corresponding materials without the incorporated ligand. This may be especially apparent using high angle annular dark field aberration-corrected scanning transmission electron microscopy due to the high contrast achieved while maintaining the resolution, thus allowing the surface as well as the bulk of the primary particles of the material to be visualised.

The reproducible physico-chemical property or characteristic of the materials of the present invention will be dependent on the application for which the material is intended. Examples of the properties that can be usefully modulated using the present invention include: dissolution (rate, pH dependence and pM dependence), disaggregation, adsorption and absorption characteristics, reactivity-inertness, melting point, temperature resistance, particle size, magnetism, electrical properties, density, light absorbing/reflecting properties, hardness-softness, colour and encapsulation properties. Examples of properties that are particularly relevant to the field of supplements, fortificants and mineral therapeutics are physico-chemical properties selected from one or more of a dissolution profile, an adsorption profile or a reproducible elemental ratio. In this context, a property or characteristic may be reproducible if replicate experiments are reproducible within a standard deviation of preferably ±10%, and more preferably ±5%, and even more preferably within a limit of ±2%. In the present invention, the phosphate binding materials preferably have reproducible phosphate binding properties and/or dissolution profiles. In addition to the physiological phosphate binding assay discussed above and exemplified in section 2.1, additional properties of the materials of the present invention, such as phosphate binding affinity or capacity, or dissolution profiles, may be also determined using techniques disclosed herein, see for example sections 2.2 and 3. In preferred embodiments, the capacity (K2) of the phosphate binders of the present invention is at least 1.5 mmol P/g binder, more preferably at least 2.0 mmol P/g binder, and most preferably at least 2.5 mmol P/g binder.

The dissolution profile of the solid ligand-modified poly oxo-hydroxy metal ion materials can be represented by different stages of the process, namely disaggregation and dissolution. The term dissolution is used to describe the passage of a substance from solid to soluble phase. More specifically, disaggregation is intended to describe the passage of the materials from a solid aggregated phase to an aquated phase that is the sum of the soluble phase and the aquated particulate phase (i.e. solution plus suspension phases). Therefore, the term dissolution as opposed to disaggregation more specifically represents the passage from any solid phase (aggregated or aquated) to the soluble phase.

The Ligand (L)

In the solid phase ligand-modified poly oxo-hydroxy metal ion species represented by the formula $(M_xL_y(OH)_n)$, L represents one or more ligands or anions, such as initially in its protonated or alkali metal form, that can be incorporated into the solid phase ligand-modified poly oxo-hydroxy metal ion material. In the materials described herein, at least one of the ligands is a carboxylic acid ligand, or an ionised form thereof (i.e., a carboxylate ligand), such as adipic acid or adipate. Preferably, the ligand is a dicarboxylic acid ligand, and may be represented by the formula HOOC—$R_1$—COOH (or an ionised form thereof), where $R_1$ is an optionally substituted $C_{1-10}$ alkyl, $C_{1-10}$ alkenyl or $C_{1-10}$ alkynyl group. In general, the use of ligands in which $R_1$ is a $C_{1-10}$ alkyl group, and more preferably is a $C_{2-6}$ alkyl group, is preferred. Preferred optional substituents of the $R_1$ group include one or more hydroxyl groups, for example as present in malic acid. In preferred embodiments, the $R_1$ group is a straight chain alkyl group. A more preferred group of carboxylic acid ligands include adipic acid (or adipate), glutaric acid (or glutarate), pimelic acid (or pimelate), succinic acid (or succinate), and malic acid (or malate). Whether the carboxylic acid ligand is present as the acid or is partially or completely ionised and present in the form of a carboxylate anion will depend on a range of factors such as the pH at which the material is produced and/or recovered, the use of post-production treatment or formulation steps and how the ligand becomes incorporated into the poly oxo-hydroxy metal ion material. In some embodiments, at least a proportion of the ligand will be present in the carboxylate form as the material are typically recovered at pH>4 and because the interaction between the ligand and the positively charged iron would be greatly enhanced by the presence of the negatively charged carboxylate ion. For the avoidance of doubt, the use of carboxylic acid ligands in accordance with the present invention covers all of these possibilities, i.e. the ligand present as a carboxylic acid, in a non-ionised form, in a partially ionised form (e.g., if the ligand is a dicarboxylic acid) or completely ionised as a carboxylate ion, and mixtures thereof.

Typically, ligands are incorporated in the solid phase poly oxo-hydroxy metal ion materials to aid in the modification of a physico-chemical property of the solid material, e.g. as compared to a poly oxo-hydroxylated metal ion species in which the ligand(s) are absent. In some embodiments of the present invention, the ligand(s) L may also have some buffering capacity. Examples of ligands that may be employed in the present invention include, but are by no means limited to: carboxylic acids such as adipic acid, glutaric acid, tartaric acid, malic acid, succinic acid, aspartic acid, pimelic acid, citric acid, gluconic acid, lactic acid or benzoic acid; food additives such as maltol, ethyl maltol or vanillin; 'classical anions' with ligand properties such as bicarbonate, sulphate and phosphate; mineral ligands such as silicate, borate, molybdate and selenate; amino acids such as tryptophan, glutamine, proline, valine, or histidine; and nutrient-based ligands such as folate, ascorbate, pyridoxine or niacin or nicotinamide. Typically ligands may be well recognised in the art as having high affinity for a certain metal ion in solution or as having only low affinity or not be typically recognised as a ligand for a given metal ion at all. However, we have found that in poly oxo-hydroxy metal ion materials, ligands may have a role in spite of an apparent lack of activity in solution. Typically, two ligands of differing affinities for the metal ion are used in the production of these materials although one, two, three, four or more ligands may be useful in certain applications.

For many applications, ligands need to be biologically compatible under the conditions used and generally have one or more atoms with a lone pair of electrons at the point of reaction. The ligands include anions, weak ligands and strong ligands. Ligands may have some intrinsic buffering capacity during the reaction. Without wishing to be bound by a particular explanation, the inventors believe that the ligands have two modes of interaction: (a) substitution of oxo or hydroxy groups and, therefore, incorporation with a largely covalent character within the material and (b) non-specific adsorption (ion pair formation). These two modes likely relate to differing metal-ligand affinities (i.e. strong ligands for the former and weak ligands/anions for the latter). There is some evidence in our current work that the two types of ligand are synergistic in modulating dissolution characteristics of the materials and, perhaps, therefore, in determining other characteristics of the material. In this case, two ligand types are used and at least one (type (a)) is demonstrable as showing metal binding within the material. Ligand efficacy, probably especially for type (b) ligands, may be affected by other components of the system, particularly electrolyte.

The ratio of the metal ion(s) to the ligand(s) (L) is also a parameter of the solid phase ligand-modified poly oxo-hydroxy metal iron material that can be varied according to the methods disclosed herein to vary the properties of the materials. Generally, the useful ratios of M:L will be between 10:1, 5:1, 4:1, 3:1, 2:1 and 1:1 and 1:2, 1:3, 1:4, 1:5 or 1:10.

Producing and Processing the Phosphate Binders

Generally, the phosphate binders of the present invention may be produced by a process comprising:
(a) mixing the solution comprising $Fe^{3+}$ and a carboxylic acid ligand, and optionally any further ligands or other components, in a reaction medium at a first pH(A) at which the components are soluble;
(b) changing the pH(A) to a second pH(B) to cause a solid precipitate or a colloid of the ligand-modified poly oxo-hydroxy metal ion material to be formed;
(c) separating, and optionally drying and/or formulating, the solid ligand-modified poly oxo-hydroxy metal ion material produced in step (b).

Examples of conditions that may be employed include the following using a first pH(A) which is less than 2.0 and the second pH(B) which is between 3.0 and 12.0, preferably between 3.5 and 8.0, and more preferably between 4.0 and 6.0, and carrying out the reaction at room temperature (20-25° C.). In general, it is preferred that in step (a), the solution contains 20 to 100 mM $Fe^{3+}$ and 50 to 250 mm of a suitable carboxylic acid ligand, and more preferably about 40 mM $Fe^{3+}$ and about 100 mM of the ligand. A preferred ligand is adipic acid.

The separation of a candidate material may then be followed by one or more steps in which the material is characterised or tested. By way of example, the testing of the phosphate binding material may be carried out in vitro or in vivo to determine one or more properties of the material, most notably its dissolution profile and/or one or more phosphate binding properties. Alternatively or additionally, the process may comprise chemically, e.g. through a titration process, or physically, e.g. through a micronizing process, altering the final particle size of the ferric iron composition and/or subjecting the ferric iron phosphate binder to one or more further processing steps on the way to producing a final composition, e.g. for administration to a subject. Examples of further steps include, but are not limited to: washing, centrifugation, filtration, spray-drying, freeze-drying, vacuum-drying, oven-drying, dialysis, milling, granulating, encapsulating, tableting, mixing, compressing, nanosizing and micronizing.

In some embodiments, additional steps may be carried out between the initial production of the material and any subsequent step in which it is formulated as a medicament. These additional post-production modification steps may include the step of washing the material, for example with water or a solution containing a further ligand such as nicotinamide, that the inventors have found to remove impurities or replace an incorporated ligand with the further ligand, thereby increasing the $Fe^{3+}$ content of the material and its phosphate binding capacity and/or providing the material with one or more further properties because of the presence of the further ligand. The effect of this is demonstrated in the examples and is discussed further in the section below.

Hydroxy and Oxo Groups

The present invention may employ any way of forming hydroxide ions at concentrations that can provide for hydroxy surface groups and oxo bridging in the formation of these poly oxo-hydroxy materials. Examples include but are not limited to, alkali solutions such as sodium hydroxide, potassium hydroxide and sodium bicarbonate, that would be added to increase [OH] in an ML mixture, or acid solutions such as mineral acids or organic acids, that would be added to decrease [OH] in an ML mixture.

The conditions used to produce the phosphate binding compositions of the present invention may be tailored to control the physico-chemical nature of the precipitate, or otherwise assist in its collection, recovery or formulation with one or more excipients. This may involve purposeful inhibition of agglomeration, or the used drying or grinding steps to subsequently affect the material properties. However, these are general variables to any such system for solid extraction from a solution phase. After separation of the precipitated material, it may optionally be dried before use or further formulation. The dried product may, however, retain some water and be in the form of a hydrated solid phase ligand-modified poly oxo-hydroxy metal ion material. It will be apparent to those skilled in the art that at any of the stages described herein for recovery of the solid phase, excipients may be added that mix with the ligand-modified poly oxo-hydroxy metal ion material but do not modify the primary particle and are used with a view to optimising formulation for the intended function of the material. Examples of these could be, but are not limited to, glycolipids, phospholipids (e.g. phosphatidyl choline), sugars and polysaccharides, sugar alcohols (e.g. glycerol), polymers (e.g. polyethyleneglycol (PEG)) and taurocholic acid.

In other embodiments, further ligands may be included in the reaction for producing the ligand-modified poly oxo-hydroxy metal ion materials, so that these ligands become incorporated into the material. Examples of ligands that may be included in this way include phosphate uptake inhibitors and/or a substance capable of providing additional therapeutic or physiological properties such as protection of the gut mucosa, for example to ameliorate potential gastric side effects that may occur on administration of the phosphate binding material to a subject. Alternatively or additionally a phosphate uptake inhibitor and/or a substance capable of ameliorating gastric side effects may be formulated in a composition with the solid ligand-modified poly oxo-hydroxy metal ion material, i.e. mixed with the material as described in the section below.

By way of illustration, phosphate uptake inhibitors are well known in the art and include nicotinamide, niacin or the inhibitors described in US 2004/0019113, US 2004/0019020 and WO 2004/085448. Examples of substances capable of ameliorating gastric side effects include retinol and/or riboflavin, see Ma et al., J. Nutr. Sci., 138(10): 1946-50, 2008.

Formulations and Uses

The solid phase materials of the present invention may be formulated for use as phosphate binding materials and may be used to treat hyperphosphatemia, in vitro and/or in vivo. Accordingly, the compositions of the present invention may comprise, in addition to one or more of the solid phase materials of the invention, a pharmaceutically acceptable excipient, carrier, buffer, stabiliser or other materials well known to those skilled in the art. Such materials should be non-toxic and should not significantly interfere with the efficacy of the solid phase materials for the application in question.

The precise nature of the carrier or other component may be related to the manner or route of administration of the composition. These compositions may be delivered by a range of delivery routes including, but not limited to: gastrointestinal delivery, especially orally and nasogastric delivery; parenteral delivery, including injection; or by implant at specific sites, including prosthetics that may be used for this purpose or mainly for another purpose but have this benefit.

The compositions described herein may also be employed for removing phosphate from food-stuffs prior to consumption or for selectively removing phosphate from dialysis fluids, plasma and whole blood. In particular, the compositions can be used in dialysis fluids to enhance phosphate removal during haemodialysis processes. Pharmaceutical compositions for oral administration may be in a tablet, capsule, powder, gel, liquid form, sprinkle or a suitable food-stuff. A tablet may include a solid carrier such as gelatin or an adjuvant. Capsules may have specialised properties such as an enteric coating. Liquid pharmaceutical compositions generally include a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included. Where the solid ligand-modified poly oxo-hydroxy ferric ion material of the present invention needs to be maintained in a solid form, e.g. to control the delivery of a component of the material, it may be necessary to select components of the formulation accordingly, e.g. where a liquid formulation of the material is made. Where the material is administered with a food-stuff, the formulation components will be chosen to be compatible with the phosphate binder material and to provide suitable physicochemical and organoleptic characteristics.

For intravenous, cutaneous or subcutaneous injection, or injection at the site of affliction, the active ingredient will be in the form of a parenterally acceptable aqueous solution or suspension which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives may be included, as required.

The materials and compositions used in accordance with the present invention that are to be given to an individual are preferably administered in a "prophylactically effective amount" or a "therapeutically effective amount" (as the case may be, although prophylaxis may be considered therapy), this being sufficient to show benefit to the individual clinical state. The actual amount administered, and rate and time-course of administration, will depend on the nature and severity of what is being treated. By way of example, phosphate binders of the present invention may be administered in amounts between about 1 and 20 g/day per patient, more preferably between about 2 and 10 g/day per patient and most preferably 3 to 7 g/day per patient. Prescription of treatment, e.g. decisions on dosage etc, is within the responsibility of general practitioners and other medical doctors, and typically takes account of the disorder to be treated, the condition of the individual patient, the site of delivery, the method of administration and other factors known to practitioners. Examples of the techniques and protocols mentioned above can be found in Remington's Pharmaceutical Sciences, 20th Edition, 2000, Lippincott, Williams & Wilkins. A composition may be administered alone or in combination with other treatments, either simultaneously or sequentially, dependent upon the condition to be treated.

The phosphate binders disclosed herein may be employed for the treatment of hyperphosphatemia. This condition often arises in renal disease, especially in patients undergoing haemodialysis and/or patients having chronic or end stage renal disease. As mentioned in the introduction, current therapies for hyperphosphatemia suffer from a number of serious disadvantages, most significantly that the prior art compositions have non-specific modes of action not restricted to phosphate or cause side effects or have long term safety issues.

The conditions that may be treated with the compositions of the present invention include high plasma phosphorus levels, hyperphosphatemia arising from any level of renal insufficiency, acute renal failure, chronic renal failure, and/or end-stage renal disease, including conditions that require haemodialysis. The clinical management of these conditions using the present invention may help to ameliorate complications associated with these conditions, such as secondary hyperthyroidism, soft tissue calcification, osteodystrophy, hypercalcaemia, hyperparathyroidism reduction, cardiovascular morbidity or mortality, renal osteodystrophy and/or calciphylaxis.

Materials and Methods
In Vitro Phosphate Binding Assay
a) Phosphate Binding at Physiological Concentration A solution containing 10 mM phosphate, a physiologically relevant concentration, and 0.9% NaCl was adjusted to pH 3, pH 5 and finally pH 7. The mass of binder was kept constant. The percentage of phosphate binding was calculated according to:

$$\text{Phosphate binding} = (1-([P]t0-[P]ti)/[P]ti) \times 100$$

Where $[P]t0$ is the concentration of phosphorus in the initial solution and $[P]ti$ is the concentration of phosphorus in filtrate at different time points.

b) Langmuir Isotherms

The Langmuir isotherms were obtained using the same methodology as in Autissier et al. (2007), except in vitro solutions also contained 0.9% NaCl to make the assay better simulate physiological conditions. These Langmuir isotherms were generated at pH 5 and experimental conditions were similar to those in "Phosphate binding at physiological concentration" except the mass of binders was varied from 13.4-80.4 mg.

In Vitro Gastrointestinal Digestion Assay

An amount of the solid ligand-modified poly oxo-hydroxy ferric ion materials or unmodified ferric oxo-hydroxide, equivalent to 60 mg elemental iron, were added to a synthetic gastric (stomach) solution (50 mL of 2 g/L NaCl, 0.15 M HCl and 0.3 mg/mL porcine pepsin) and incubated at 37° C. for 30 minutes with radial shaking. Then 5 mL of the resulting gastric mixture was added to 30 mL of synthetic duodenal solution (containing 10 g/L pancreatin and 2 g/L NaCl in 50 mM bicarbonate buffer pH 9.5). The final volume was 35 mL and the final pH was 7.0. The mixture was incubated at 37° C. for 60 min with radial shaking. Homogeneous aliquots (1 mL) were collected at different time points during the process and centrifuged at 13,000 rpm for 10 minutes to separate the aggregate and aquated disaggregated phases. The supernatant was analysed for iron content by ICPOES. At the end of the experiment, the remaining solution was centrifuged at 4,500 rpm for 15 min and the supernatant analysed for the Fe content by ICPOES. The mass of remaining material (i.e. the wet pellet) was recorded. Concentrated $HNO_3$ was added to this wet pellet and the new mass recorded. The tubes were left at room temperature until all the pellet dissolved and an aliquot was collected for ICPOES analysis to determine the quantity of iron that did not disaggregate/dissolve. The starting amount of iron was calculated from the iron in the wet pellet plus the iron in the supernatant.

To differentiate between soluble iron and aquated particulate iron in the supernatant, at each time point, this fraction was also ultrafiltered (Vivaspin 3,000 Da molecular weight cut-off polyethersulfone membrane, Cat. VS0192, Sartorius Stedium Biotech GmbH, Goettingen, Germany) and again analysed by ICPOES.

Inductively Coupled Plasma Optical Emission Spectrometry Analysis (ICPOES)

Iron and phosphorus contents of solutions or solids (including wet solids) were measured using a JY2000-2 ICPOES (Horiba JobinYvon Ltd., Stanmore, U.K.) at the iron specific wavelength of 259.940 nm, and at the phosphorus wavelengths of 177.440 and/or 214.914 nm. Solutions were diluted in 1-7.5% nitric acid prior to analysis while solids were digested with concentrated $HNO_3$. The percentage of iron in solution or solid phase was determined by the difference between the starting iron content and either the iron in the soluble phase or the iron in the solid phase depending on the assay.

Determination of Particle Size

The size distribution of micron-sized particles was determined using a Mastersizer 2000 with a Hydro-uP dispersion unit (Malvern Instruments Ltd, Malvern, UK) and nano-sized particles was determined with a Zetasizer Nano ZS (Malvern Instruments Ltd, Malvern, UK). Mastersizer measurements required no sample pre-treatment whereas centrifugation was needed to remove large particles prior to Zetasizer measurements.

Infrared Analysis (IR)

IR spectra were collected using a DurasamplIR diamond ATR accessory with a Nicolet Avatar 360 spectrometer with a wavelength range of 4000-650 $cm^{-1}$ and resolution of 4 $cm^{-1}$. Analysis were undertaken by ITS Testing Services (UK) Ltd Sunbury on Thames, UK.

Transmission Electron Microscopy and Energy Dispersive X-ray Analysis (EDX)

Powder samples were analysed by first dispersing the powder in methanol and then drop-casting on standard holey carbon TEM support films. Analyses were undertaken by the Institute for Materials Research, University of Leeds, UK.

Exploratory Human Study to Assess Phosphate Binding of FeOH Ad100

As part of a study assessing markers of oxidative damage and antioxidant status after oral iron supplementation, a study was carried out to determine whether dietary phosphate ($PO_4$) binding could be observed for phosphate binders of the present invention (893 mg) when given with a meal (containing 781.5 mg phosphorus (P)). Briefly 13 volunteers, each received a high-P breakfast on 3 occasions with either placebo or the phosphate binder or ferrous sulphate—these being given in random order. Urine was collected pre-meal (spot urine), at 0-3 hours post meal (expect little or no urinary phosphate derived from the meal) and at 3-8 hours post meal (expect ≈45% of absorbed phosphate that was derived from the meal to be excreted.

Results

1. Production of Phosphate Binder

Broadly, the phosphate binders described herein were produced by totally, or partially, neutralising an acidic solution, typically at pH<2.5, containing, at least, soluble ferric and one or more ligands. Subsequently, a ligand-modified oxo-hydroxide material was formed once a suitable pH was achieved, typically at pH>3.5, which could be recovered using a range of strategies (e.g. centrifugation). Note that the production of phosphate binders described below does not include any post-production modifications, such as washing.

1.1 FeOH Ad100

To a 500 mL beaker containing 400 mL dd$H_2O$, 4.5 g KCl and 7.3 g adipic acid were added. The mixture was stirred until all of the components dissolved. Then 100 mL of a ferric iron solution was added (200 nm FeCl$_3$.6H$_2$O, 1.7 mL conc. HCl in 100 mL ddH$_2$O). The final concentration of iron in the solution was 40 mM and KCl was 0.9% w/v. The pH of the final solution to which ferric iron was added is generally below <2 and usually about 1.5. To this mixture, NaOH was added drop-wise (from a 5M NaOH solution prepared in ddH$_2$O) with constant stirring until pH 4.5±0.2 (see FIG. 1). The process was carried out at room temperature (20-25° C.). The solution was then centrifuged and the agglomerate was air-dried in an oven at 45° C. The dried material was milled by hand or micronized with a ball mill.

1.2 FeOH Ad100 SiO$_2$

The procedure for producing FeOH Ad100 SiO$_2$ was the same as for FeOH Ad100 except a sodium silicate solution (SiO$_2$.NaOH) was used instead of NaOH to raise the pH. This solution contains 27% Si.

1.3 FeOH Glutaric100

The procedure for producing FeOH Glutaric100 was the same as for FeOH Ad100 except 6.6 g glutaric was used instead of adipic acid and NaOH was added until pH 5.0±0.2 was reached.

1.3 FeOH Pimelic100

The procedure for producing FeOH Pimelic100 was the same as for FeOH Ad100 except 8.0 g pimelic was used instead of adipic acid and NaOH was added until pH 4.2±0.2 was reached.

2. In Vitro Phosphate-binding 2.1 P-Binding at Physiological Concentration

Figure 2A:
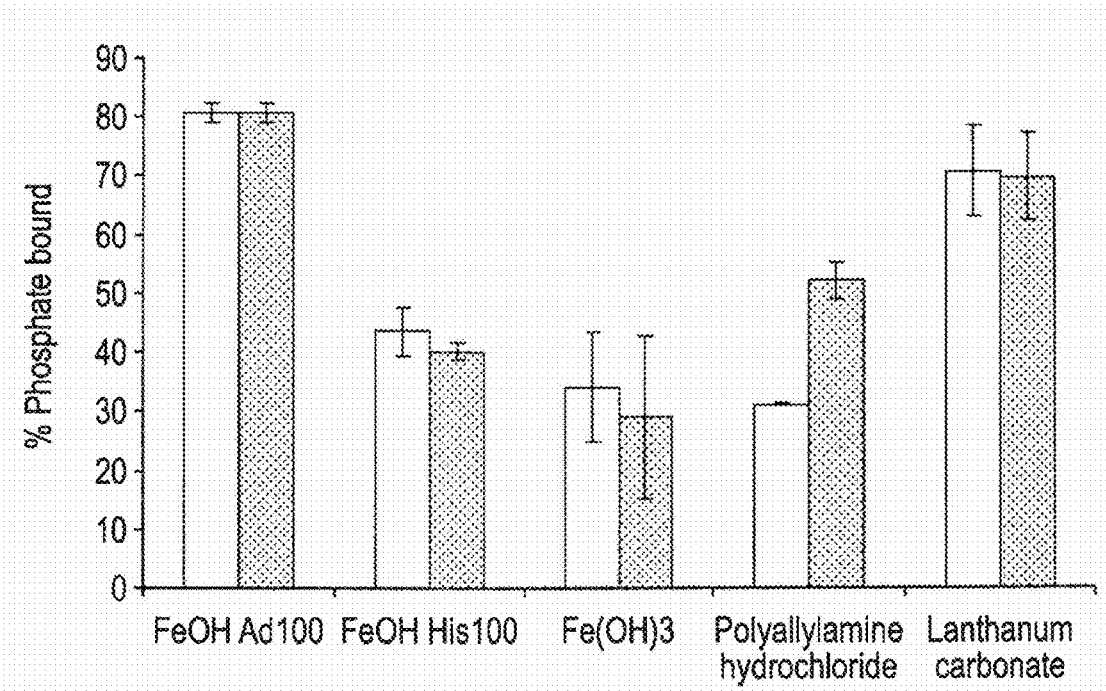
FIG. 2: (a) In vitro phosphate binding. When iron hydroxide is ligand-modified as described (e.g. FeOH Ad100) there is clearly superior phosphate binding to unmodified ferrihydrite ($Fe(OH)_3$) or Renagel (polyallylamine hydrochloride) and at least equivalence to the effective, but potentially toxic, lanthanum carbonate. Moreover, the ligand chosen is advantageous with others, for example histidine, which unlike adipate does not lead to the marked increase in phosphate binding (i.e. FeOH His100 versus $Fe(OH)_3$). White bars are pH 3 and grey bars are pH 5. (b) A second example of in vitro phosphate binding: pH3 (white), pH5 (grey) and also at pH 7 (black). The effectiveness of Fe OH Ad100 $SiO_2$ (i.e. silicate modified FeOH Ad100) is also shown. In both figures (a and b) the solution was 10 mM phosphate and the amount of binder used was 53.6 mg in a total volume of 20 ml. In these experiments the binder was first exposed to the lower pH for 60 minutes then the higher pH(s) for 60 minutes, all sequentially.
Figure 2B:
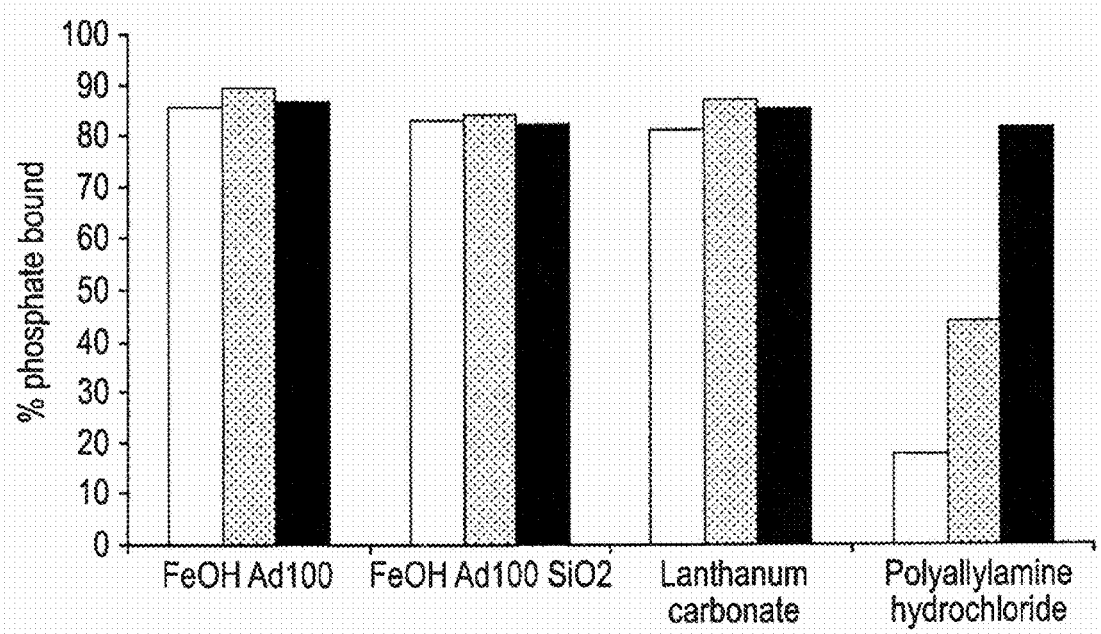

The iron oxide ferrihydrite is well known to bind phosphate. For example, following incubation at pH 3 for 60 minutes and then pH 5 for 60 minutes, 54 mg ferrihydrite will bind about 30% of phosphate from a 20 mL, 10 mM phosphate solution (FIG. 2a). On a small scale this may mimic physiological conditions in the use of phosphate binders. A preferred amount of binding is ≈50% under identical conditions as seen for the commercial phosphate binder Renagel, polyallylamine hydrochloride (FIGS. 2a/b). A yet more preferred amount is 70-85% under identical conditions, as seen in the high affinity phosphate binding agent lanthanum carbonate (FIGS. 2a/b). FeOHAd100 and FeOHAd100 SiO$_2$ achieve a phosphate binding of 80-85% binding under these conditions (FIGS. 2a/b) illustrating significant beneficial modification in relation to ferrihydrite alone. In FIGS. 2a and 2b, white bars relate to experiments carried out at pH 3 and grey bars pH5, and black bars are at pH7 (in FIG. 2b only), and in all cases the binder was first exposed to the lower pH for 60 minutes and then the higher pH(s) for 60 minutes, all sequentially.

Figure 3:
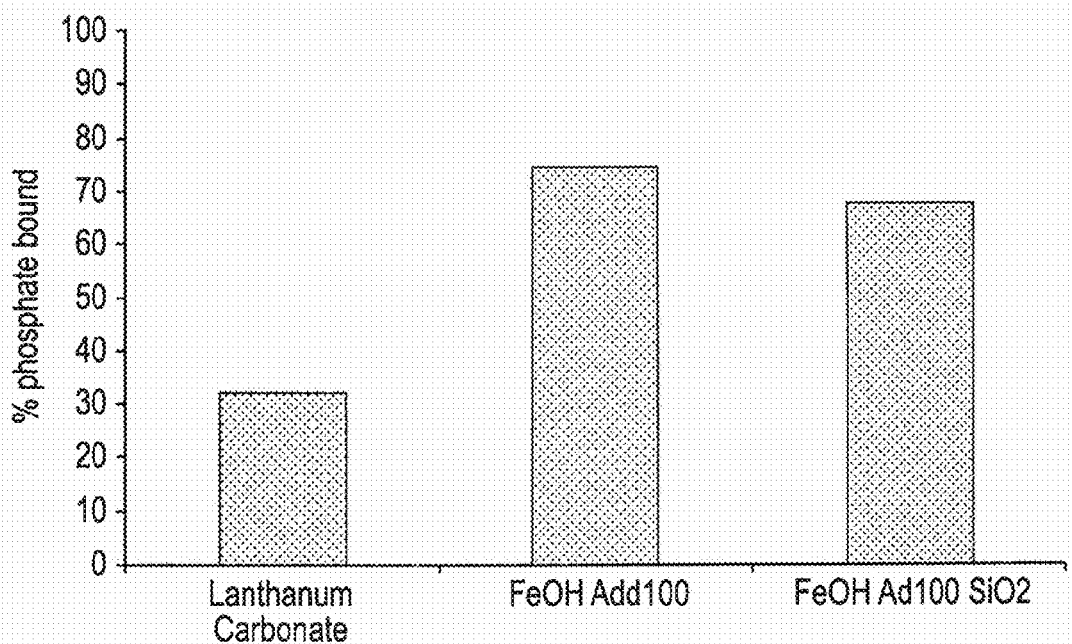
FIG. 3: Lanthanum carbonate appears only effective where low pH 'pre-conditioning' occurs unlike for FeOHAd100 and FeOH Ad100 $SiO_2$. Experimental conditions were as in FIGS. 2a/b except that the phosphate binders were only exposed to the phosphate solution at pH 5 and not sequentially and thus no acidic (gastric) pre-conditioning of the binders occurred at the higher pHs.

Interestingly, when assay conditions were changed such that the exposure of binder was made directly to the solution at pH 5 for 1 hour, but without 'pre-conditioning' at pH 3 for 1 hour, the phosphate binding fell sharply for lanthanum carbonate from 70-85% (FIG. 2) to ≈30% (FIG. 3). In contrast phosphate binding by FeOHAd100 and FeOHAd100 SiO$_2$ fell only from 80-85% (FIG. 2) to 65-75% (FIG. 3), indicating superior binding by the latter binder under conditions that may exist physiologically (e.g. post-prandial gastric pH). In the context of superiority, it is also worth noting that lanthanum carbonate can be toxic and Renagel is a non-specific binder.

2.2 Langmuir Plots—Determination of Affinity and Capacity

We further compared the phosphate binding abilities of FeOH Ad100, FeOH Ad100 SiO$_2$, and lanthanum using Langmuir isotherms. The Langmuir equation relates the adsorption of molecules on a solid surface to a concentration and was adapted to determine the affinity and capacity of the above noted phosphate binders:

$$\frac{C}{C_{ad}/m} = \frac{1}{K2}C + \frac{1}{K1\,K2}$$

$$y = a*x + b$$

C=concentration of adsorbate unbound in mM
$C_{ad}/m$=mmol of adsorbate bound per g binder
K1=affinity; K2=capacity It was not possible to determine these values for Renagel because its low affinity required a higher concentration of phosphate than the physiologically relevant concentration (10 mM) that was tested in this experiment. Langmuir isotherms were generated at pH 5 and experimental conditions were similar to those in FIGS. 2a/b, except the mass of binders was varied from 13.4-80.4 mg.

The results are shown in the Table below and demonstrate that the affinity is similar for the three compounds, but capacity is inferior for lanthanum carbonate.

| Phosphate binder | K1 (Affinity) | K2 (Capacity) |
| --- | --- | --- |
| FeOH Ad100 | 1.5 | 3.4 |
| FeOH Ad100 SiO$_2$ | 1.4 | 2.9 |
| Lanthanum Carbonate | 1.6 | 1.0 |

3. In Vitro Gastro-Intestinal Dissolution

Figure 4:
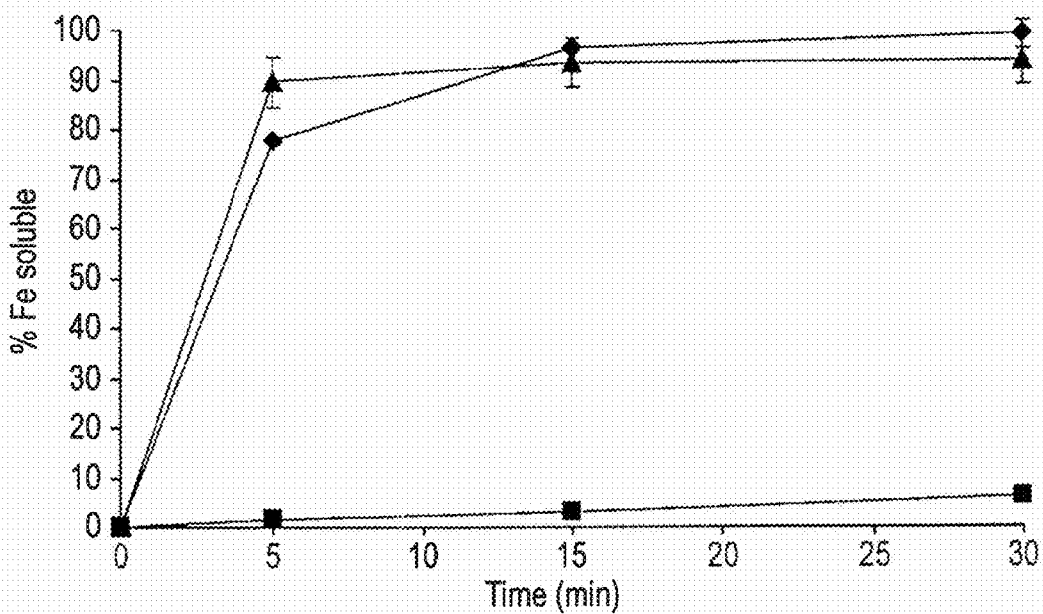
FIG. 4: Dissolution profile for FeOH Ad100 (diamonds), FeOHAd100 $SiO_2$ (triangles), and unmodified 2-line ferrihydrite (squares) at pH 1.2. See materials and methods for detailed description of methodology.

While the phosphate binding ability provides one example of how ferrihydrite has been modified herein to alter its physicochemical properties, a second example is with the dissolution profile at very acidic pH. At pH 1.2 the iron in FeOHAd100 and FeOH Ad100SiO$_2$ is rapidly dissolved while that from unmodified ferrihydrite is slowly dissolved. For beneficial application FeOHAd100 and FeOH Ad100SiO$_2$ will be ingested with food and will largely remain particulate at post-prandial pHs (pH>2.5), but these laboratory dissolution data are simply shown to illustrate that the agents claimed differ markedly from ferrihydrite (FIG. 4).

4. Particle Size Determination

Figure 5A:
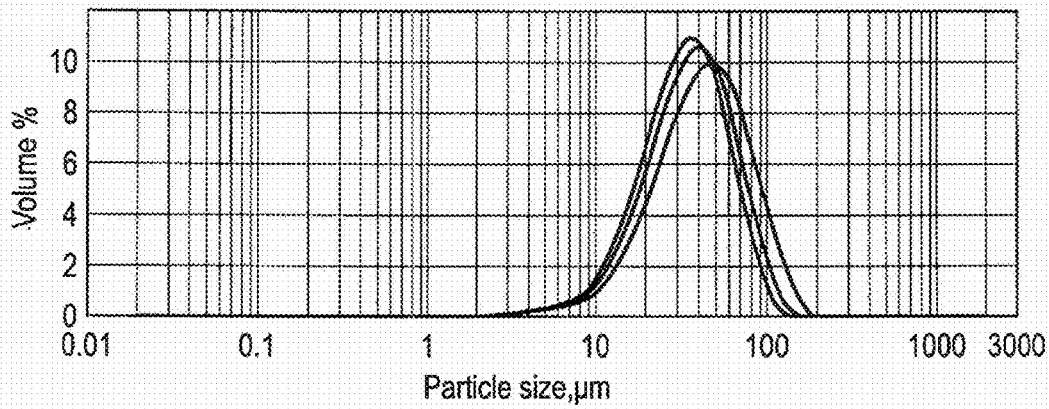
FIG. 5: Particle size of FeOHAd100 freshly prepared (a); upon drying(b); and after basic milling (c).
Figure 5B:
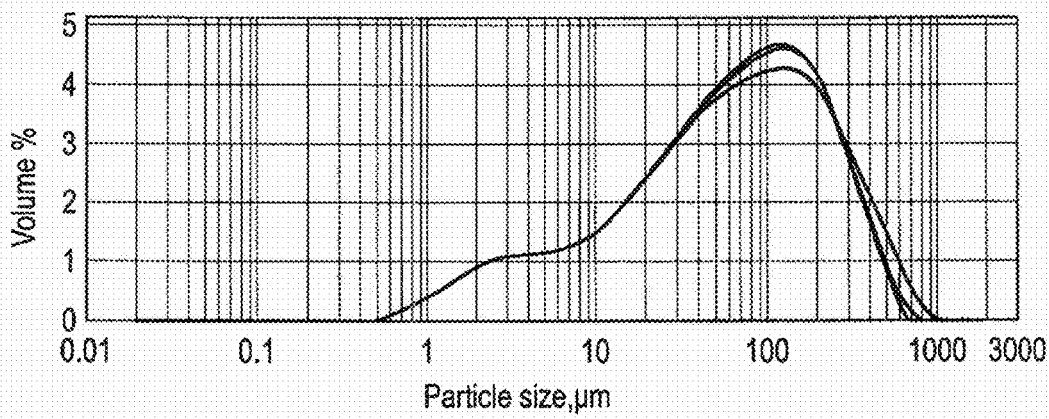
Figure 5C:
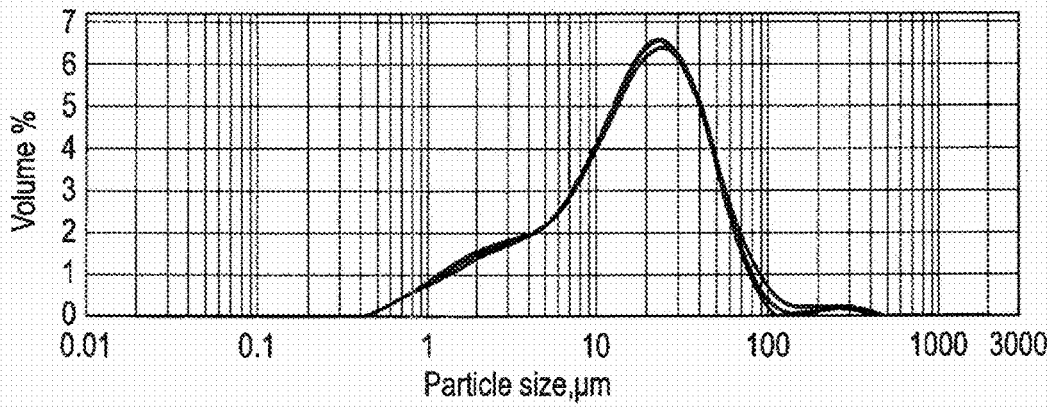

FIG. 5 shows that the agents claimed herein have an aggregated particle diameter spanning 10-100 um with a median diameter around 40 um (a); upon drying the range is increased (b), especially to larger sizes (median then >100 um) but can be restored with basic milling for example (c) or even reduced further with micronisation or nanosizing (not shown).

5. Chemical Characterisation 5.1 IR Characterisation

Figure 6:
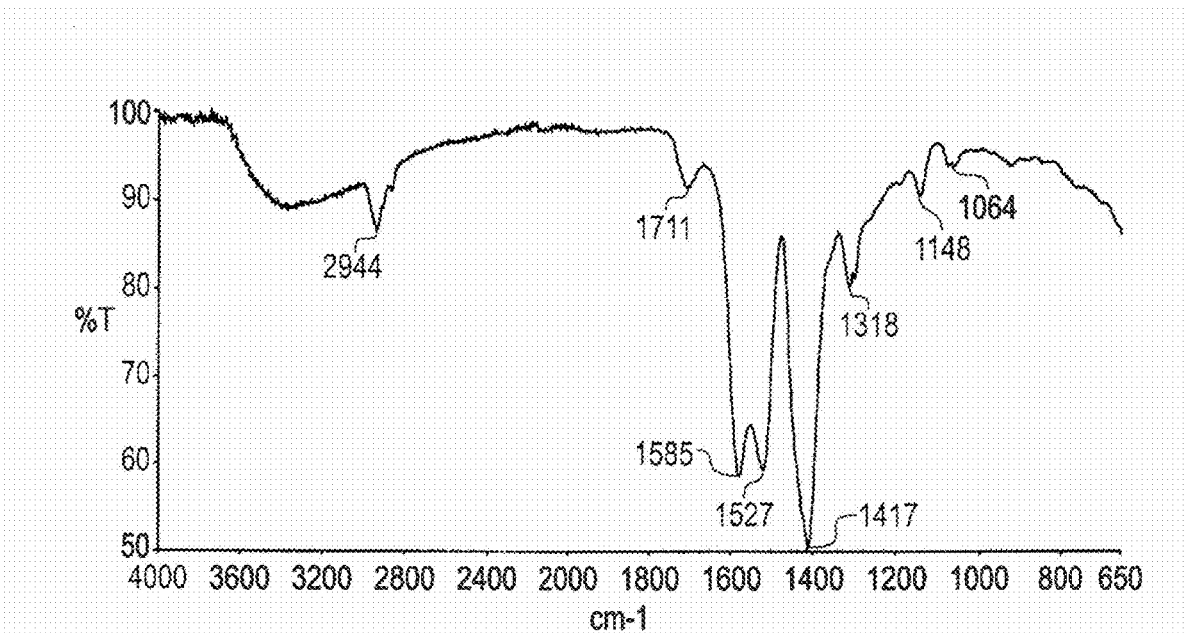
FIG. 6: Infrared analysis of FeOH Ad100.
Figure 7:
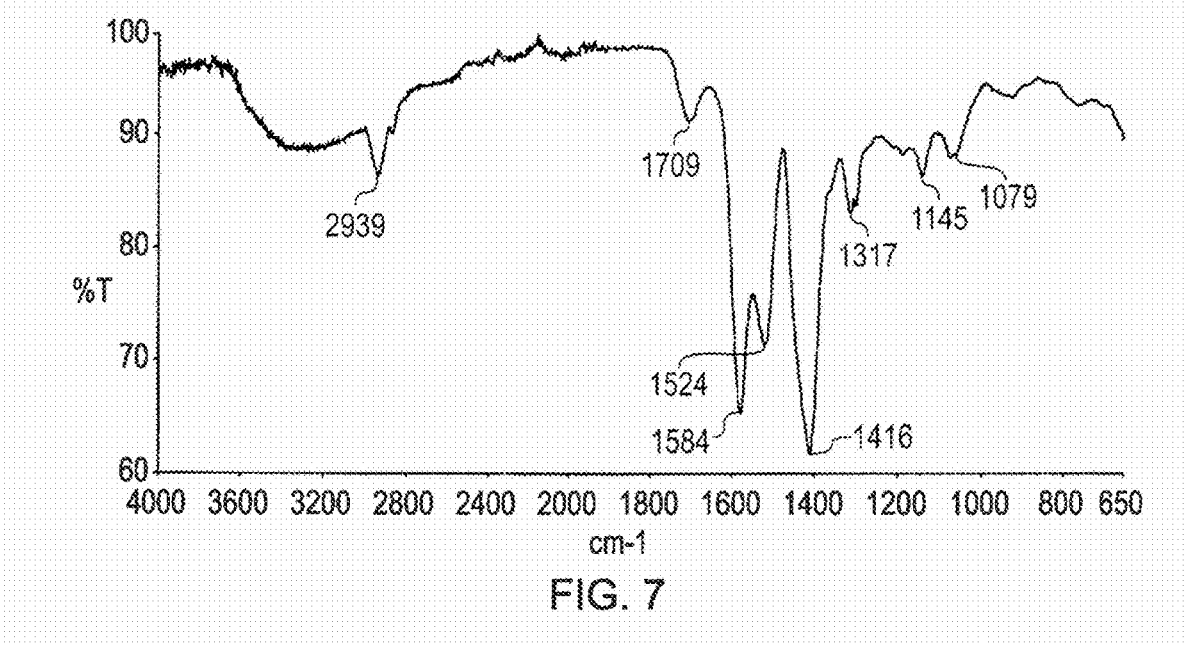
FIG. 7: Infrared analysis of FeOH Ad100 $SiO_2$.
Figure 8:
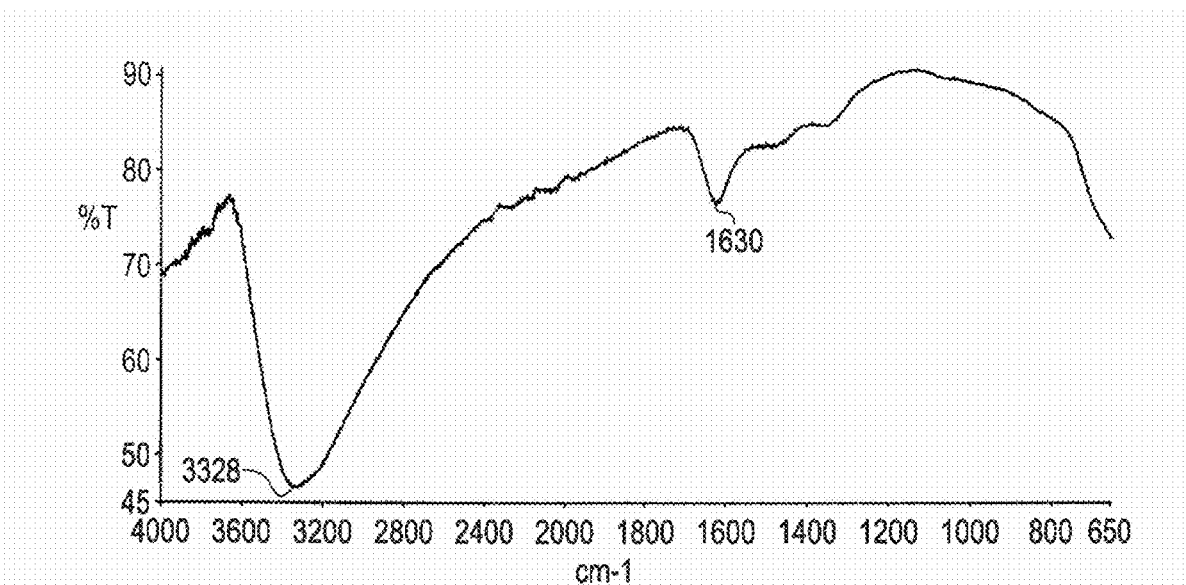
FIG. 8: Infrared analysis of unmodified ferrihydrite ($Fe(OH)_3$) for reference.
Figure 9:
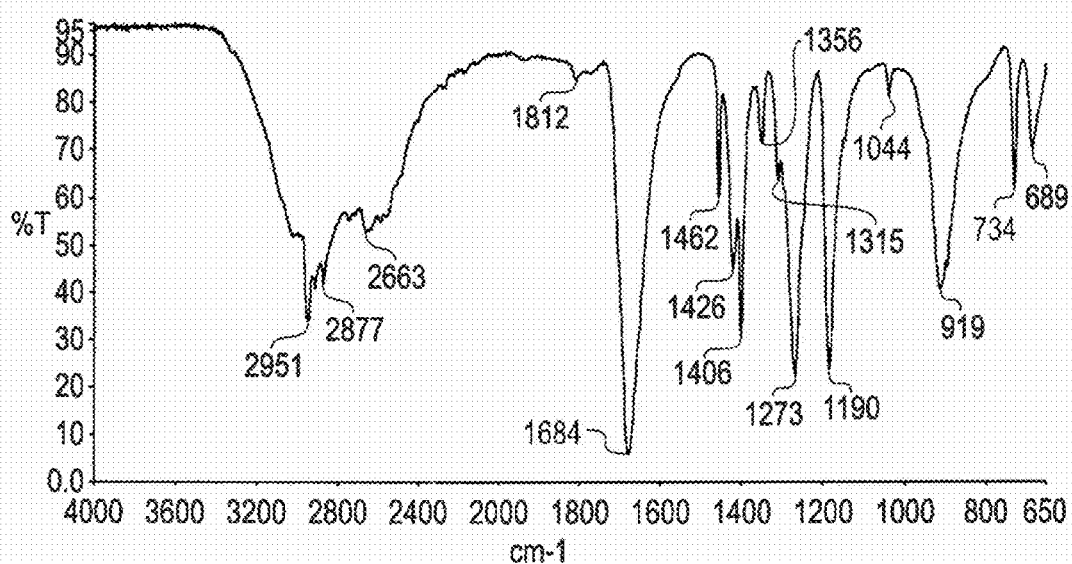
FIG. 9: Infrared analysis of unmodified adipic acid for reference.

The infrared spectra of FeOH Ad100 (FIG. 6) and FeOH Ad100 SiO$_2$ (FIG. 7) were obtained and showed the presence of two bands at 1583-1585 cm$^{-1}$ and 1524-1527 cm$^{-1}$. These are absent in either unmodified ferrihydrite (FIG. 8) or adipic acid (FIG. 9) and indicate the presence of some bonding between the carboxylate group of adipic acid (at 1684 cm$^{-1}$) and a cation, which can include iron in the FeOH Ad100 and FeOH Ad100 SiO$_2$ materials.

5.2 TEM

FeOH Ad100

Electron diffraction gave 2 diffuse rings (plane spacings at 2.5 and 1.5 Angstroms respectively); these are diagnostic for the presence of a ferrihydrite-like structure (FIG. 10b). All other forms of iron oxide such as Akageneite (β- or beta-iron oxo-hydroxide) or maghemite (γ- or gamma-iron oxide) give completely different plane spacings (see Cornell & Schwertmann, The Iron Oxides Structure, Properties, Reactions, Occurrence and Uses. 2nd ed, 1996, VCH Publishers, New York).

The general composition by EDX shows the presence of low levels of Na, Cl, and K with significant levels of Fe, O and C (FIG. 10c). The amount of C is greater than can be attributed to the carbon support film, and it is concluded that this additional C is from adipic acid. High magnification images indicate a mottled structure where the darker spots of 2-3 nm indicate a primary grain size (FIG. 10a). This structure is still consistent with 2-line ferrihydrite (Janney et al, 2000), although in general is more disordered than unmodified 2-line ferrihydrite. Thus, the phosphate binding materials described herein are agglomerated particles with a ferrihydrite-like structure of a primary crystallite size of 2-3 nm and containing Fe, O and C, and low levels of Cl, Na and K. They are therefore ligand-modified structures leading to some markedly different and, with respect to phosphate binding, beneficial properties compared to ferrihydrite alone.

6. Exploratory Human Study to Assess Phosphate Binding of FeOH Ad100

As part of a study assessing markers of oxidative damage and antioxidant status after oral iron supplementation, a study was carried out to determine whether dietary phosphate ($PO_4$) binding could be observed for phosphate binders of the present invention (893 mg) when given with a meal (containing 781.5 mg phosphorus (P)). This study was used to test the hypothesis that urinary phosphate excretion would be greater in a placebo period than the phosphate binder period and this was tested using a 1 tailed, paired T test.

Figure 11:
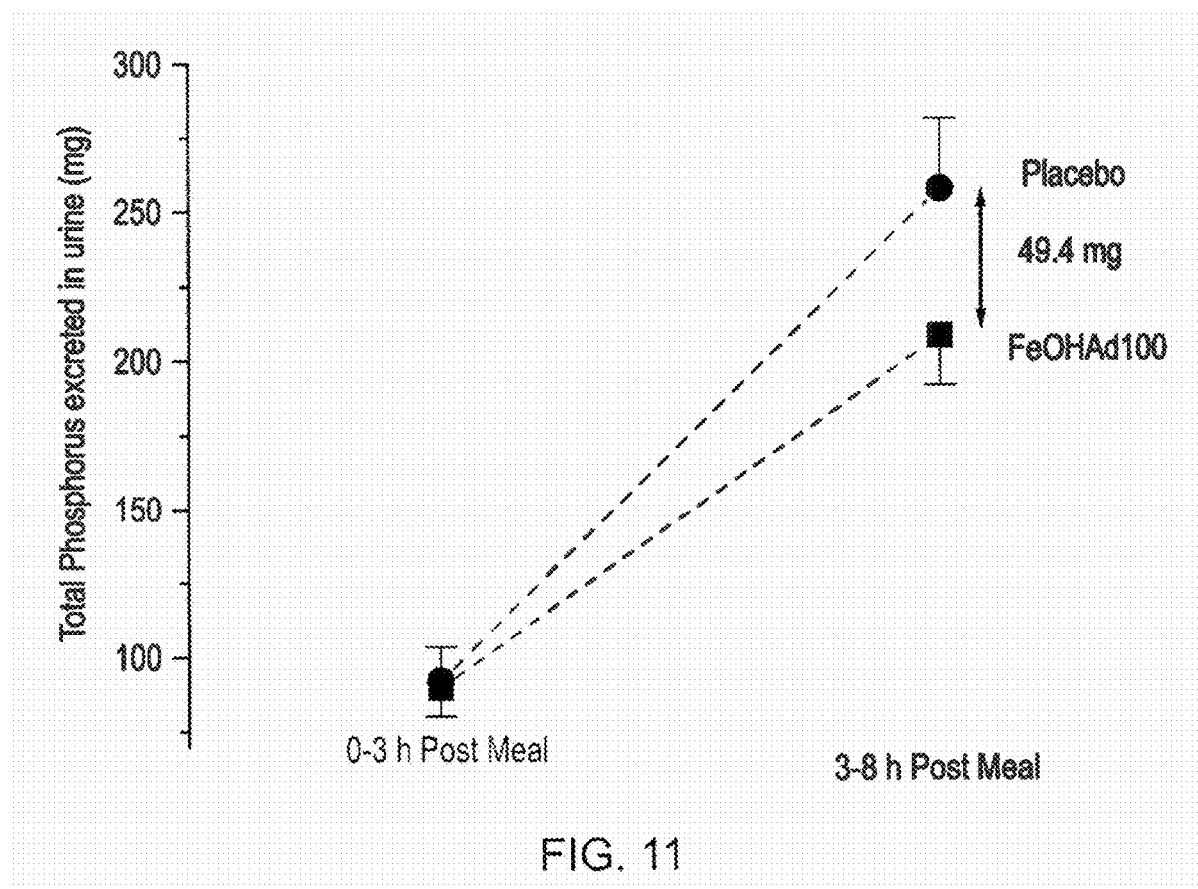
FIG. 11. Mean (SEM) Urinary Phosphorus Excretion (mg in 8 hours) from 13 Volunteers Following a Meal plus FeOH Ad100 or placebo.

First, following ingestion of the breakfast alone (i.e. just with placebo), urinary excretion of phosphorus, corrected for creatinine concentration, was used to identify the period in which there was a rise in excreted phosphate concentration. This was seen at 3-8 hours post ingestion of the meal as anticipated (data not shown). Next, at the 3-8 hour time point, phosphorus excretion was compared following the breakfast plus placebo versus breakfast plus treatment with a binder of the present invention, and a difference of 49.4 mg phosphorus was observed in excretion (p=0.01; FIG. 11).

To provide some context around these figures, the in vivo data for phosphorus binding of one material of the present invention were compared with known literature. Calculations suggest that the binder of the present invention, under these dietary conditions, binds 514 mg $PO_4$ per g of binder, once the urinary data are extrapolated from 8 h to 24 h excretion and phosphorus is converted to phosphate. This extrapolation accounts for the remaining absorbed phosphate to be excreted over the following 16 hours and assumes 70% gut absorption of phosphate from the meal (Anderson, J. J. B, Watts M. L., Garner, S. A., Calvo, M. S., and Klemmer, P. J. Phosphorus. In: Bowman, B., and Russell, R., ed. Present Knowledge in Nutrition, 9th ed. ILSI Press, 2006). This compares to known in vivo values for Sevelamer hydrochloride of 262 mg phosphate per g of binder (Sherman R A: Seminars in dialysis— Vol. 20(1), 2007, 16-18).

It should be also noted that the meal used here is, purposefully, extremely high in P (to enable a movement in urinary P to be observed), but therefore does not represents typical P intakes from a single meal by renal patients. Thus, under more typical conditions, the percentage of P bound by a phosphate binder of the present invention (or indeed any of the binders) will be higher.

7. Further Comparative Experiments with Different Ligands

Figure 12:
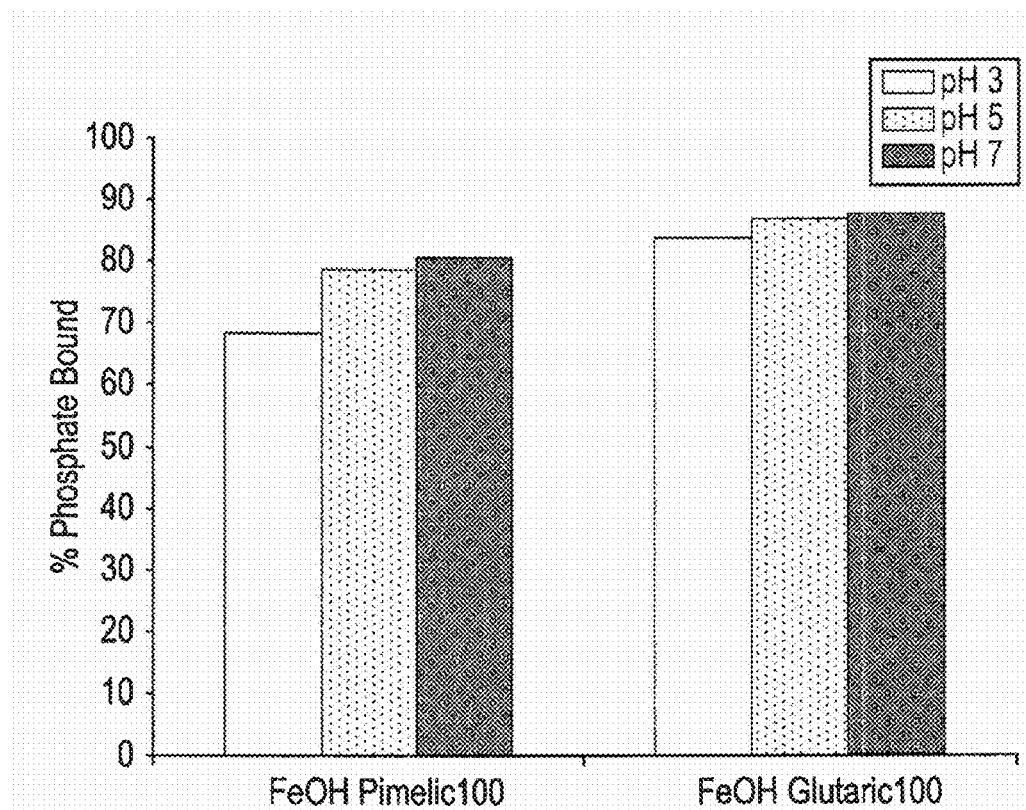
FIG. 12. In vitro phosphate binding of various ligand-modified ferric hydroxides. The solution was 10 mM phosphate and the amount of binder used was 214 mg in a total volume of 80 ml. The binder was first exposed to the lower pH for 60 minutes then the higher pH(s) for 60 minutes, all sequentially.
Figure 13:
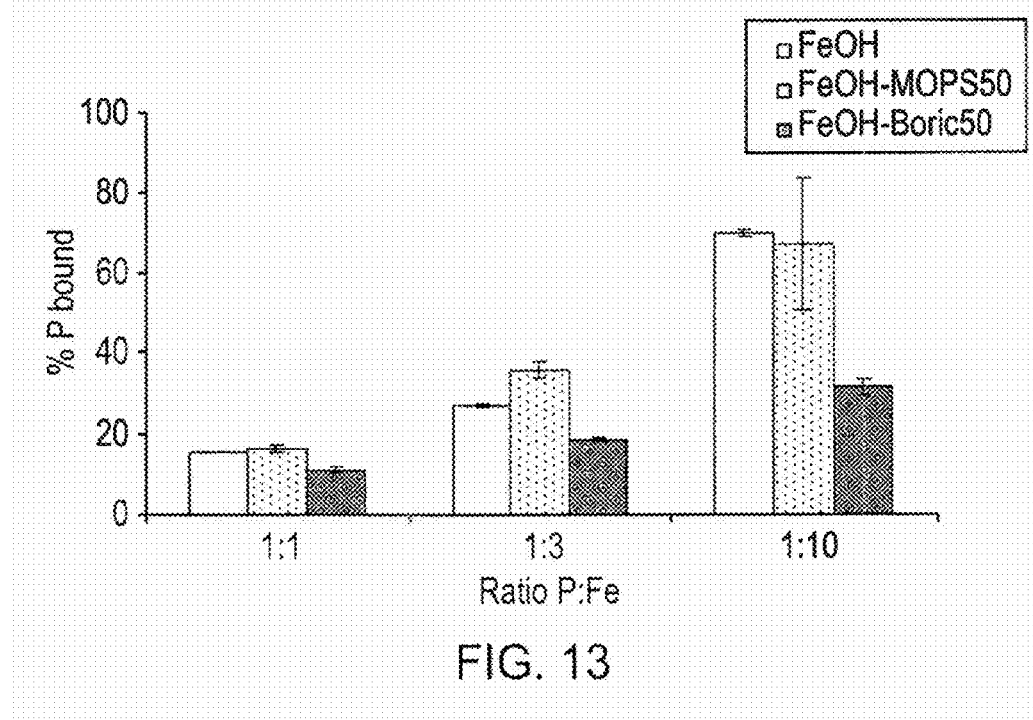
FIG. 13. In vitro phosphate binding of various ligand-modified ferric oxo-hydroxides. Different amounts of binder were added to a 10 mM phosphate solution to obtain 1:1, 1:3 and 1:10 phosphate-to-iron molar ratios. Phosphate binding occurred for 120 min at 37° C.

Further phosphate binding materials of the present invention that include a range of different carboxylic acid ligands (pimelic acid and glutaric acid) were made and compared with materials that comprise other types of ligand. These results are summarised in FIGS. 12 and 13 and show that the carboxylic acid ligands enhanced the phosphate binding capacity of the starting material, while other types of ligand either had no effect on the phosphate binding capacity of FeOH or else reduced it (see FeOH-MOPS 50 and FeOH Boric 50).

8. Modelling Pill Burden

A major disadvantage of current therapeutic treatments for the removal of phosphate is the pill burden placed on patients, where the need to ingest large quantities of pills adversely affects side effects and patient compliance. Accordingly, the pill burden for some of the exemplified materials was compared to Renagel and Fosrenol using a mathematical model based on in vitro data and typical gastrointestinal conditions, such as pH, average dietary phosphorus concentration under clinical conditions, and competing anions, and the results are shown in the Table below.

TABLE

Pill burden for FeOH Ad100, Renagel and Fosrenol.

| Product | Pills/day | Typical Maintenance Dosage (g/day) | | Delivery | Comments |
| | | Formulated product | Active substance | | |
| --- | --- | --- | --- | --- | --- |
| FeOH Ad100[a] | 3 | 3.6[b] | 3.3 | Tablet or capsule | Good tolerability profile expected |
| Renagel[c] | 9 | 7.1 | 6.5 | Film-coated tablets | Low phosphate specificity and therefore unpredictable side-effects |
| Fosrenol[c] | 3 | 6.2[d] | 2.9 | Tablets must be chewed | Significant toxicity concerns |
| FeOH Ad100 – KCl + washed[e] | 3 | 3.1[b] | 2.8 | Tablet or capsule | Good tolerability profile expected |

[a] Values estimated from model based on in vitro data;
[b] Assuming formulation adds less than 10% mass as is true for Renagel;
[c] Data from literature;
[d] A 3.1 g pill contains 750 mg elemental lanthanum (1.45 g lanthanum carbonate).
[e] Values estimated by linear extrapolation of unwashed material based on the 15% increase in phosphate binding that washing produces, see below for production method.

9. Pre-Formulation Strategies: Enhancement of Iron Content

The FeOH Ad100 produced and characterised as described above was tested to determine the effect of pre-formulation processing steps, such as washing. In these experiments potassium chloride, the reaction medium used in the production of the materials, was removed from the synthesis procedure (FeOH Ad100–KCl) and a washing step of the precipitated material has been added (FeOH Ad100–KCl+washed). Both of these steps resulted in an increase in iron content in the materials produced, see the results in the Table below.

TABLE

Iron content of FeOH Ad100 recovered using various production methods.

| Product | Iron content (mg/100 mg material) |
| --- | --- |
| FeOH Ad100 | 22.6 |
| FeOH Ad100 −KCl | 24.7 |
| FeOH Ad100 −KCl +washed | 29.5 |

Figure 14:
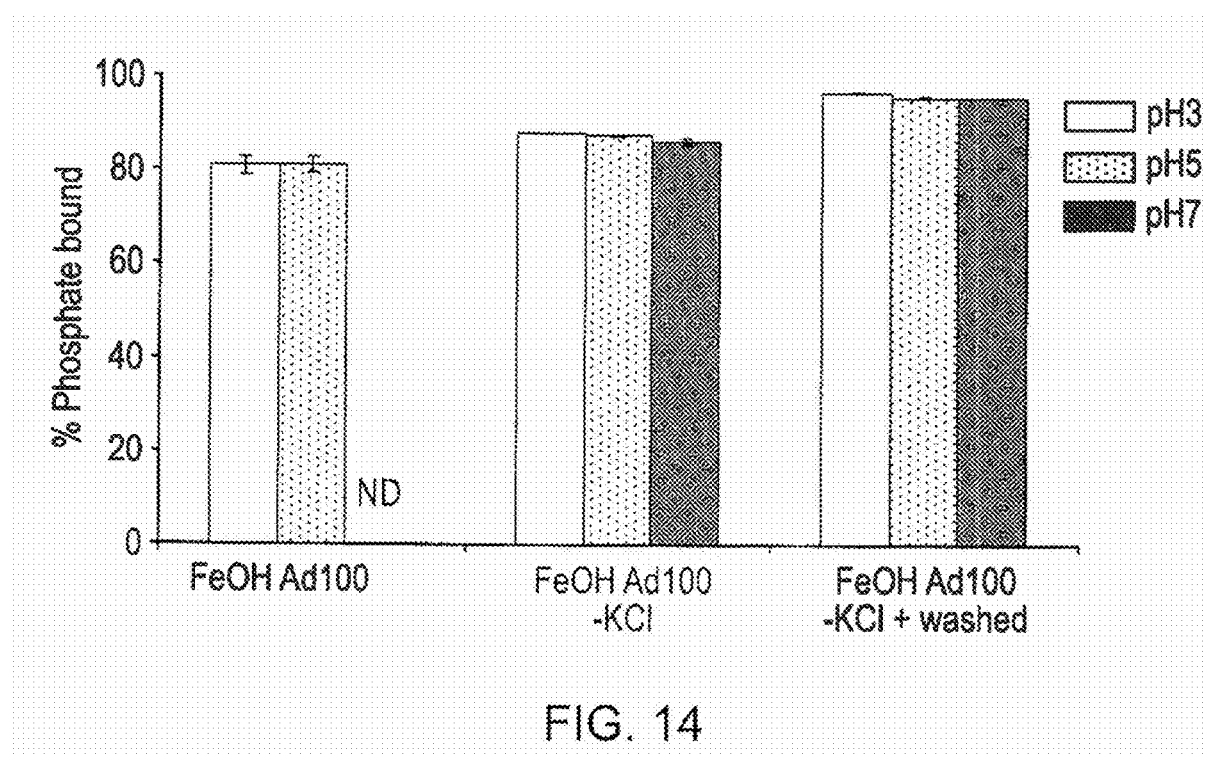
FIG. 14. In vitro phosphate binding of FeOH Ad100 recovered using different production methods. The solution was 10 mM phosphate and the amount of binder used was 214 mg in a total volume of 80 ml. The binder was first exposed to the lower pH for 60 minutes then the higher pH(s) for 60 minutes, all sequentially. (ND=Not determined).

−KCl: without KCl;
+washed: addition of a washing step Excluding KCl from the synthesis and adding a washing step also resulted in an increase in the phosphate binding ability as shown in FIG. 14.

When FeOH Ad100−KCl and FeOH Ad100−KCl+washed were tested and their phosphate binding under a range of phosphate: binder ratios was compared, the results were consistent with those shown in FIG. 14 and confirmed the increase in phosphate binding due to the washing step.

10. Ligand Replacement

Work in which the adipic acid of FeOH Ad100 was replaced by a different ligand was also carried out. This consisted in either washing FeOH Ad100 with a nicotinamide solution (FeOH Ad100+nicotinamide wash) or adding nicotinamide during the precipitation process, after the formation of FeOH Ad100 primary particles (producing FeOH Ad100+ nicotinamide agglomeration instead of FeOH Ad100+adipate agglomeration). Both strategies resulted in a decrease of adipic acid content (below) and, although there was a reduction in phosphate binding, these materials may be useful for the treatment of hyperphosphatemia by combining phosphate binding with the release of nicotinamide, which is known to reduce active uptake of phosphate in the gut.

TABLE

Adipic acid content of FeOH Ad100 recovered using various ligand replacement methods. All materials were produced in the absence of KCl.

| Product | Adipic acid content (mg/100 mg material) |
| --- | --- |
| FeOH Ad100 | 70.0 |
| FeOH Ad100 +nicotinamide wash | 52.9 |
| FeOH Ad100 +nicotinamide agglomeration | 44.3 |

REFERENCES

All publications, patent and patent applications cited herein or filed with this application, including references filed as part of an Information Disclosure Statement are incorporated by reference in their entirety.

U.S. Pat. No. 6,903,235.
U.S. Pat. No. 6,174,442.
WO 2007/088343.
WO 2008/071747.
Autissier V, Damment S J P, Henderson R A: Relative in vitro efficacy of the phosphate binders lanthanum carbonate and sevelamer hydrochloride. J. Pharm. Sci., 96: 2818-2827, 2007.
Drits et al., Structural Model for Ferrihydrite. Clay Minerals, 28: 185-207, 1993.
Janney et al., Transmission electron microscopy of synthetic 2- and 6-line ferrihydrite, Clays and Clay Minerals, 48: 111-119, 2000.
Mavrocordatos and Fortin, Quantitative characterization of biotic iron oxides by analytical electron microscopy, American Mineralogist, 87: 940-946, 2002.
Pan et al., Electron beam damage studies of synthetic 6-line ferrihydrite and ferritin molecule cores within a human liver biopsy, Micron, 37: 403-411, 2006.
Michel et al., The Structure of Ferrihydrite, a Nanocrystalline Mineral, Science, 316: 1726, 2007.
Cornell & Schwertmann, The Iron Oxides Structure, Properties, Reactions, Occurrence and Uses. 2nd ed, 1996, VCH Publishers, New York.

The invention claimed is:

1. A method of treating hyperphosphatemia, or a complication or secondary condition that results from hyperphosphatemia, the method comprising administering to a patient in need thereof a therapeutically effective amount of a phosphate binder that comprises a ferric iron composition that is a solid ligand-modified poly oxo-hydroxy metal ion material represented by the formula $(M_xL_y(OH)_n)$, wherein M represents one or more metal ions that comprise $Fe^{3+}$ ions, L represents one or more ligands that comprise a carboxylic acid ligand, or an ionised form thereof, and OH represents oxo or hydroxy groups and wherein the material has a polymeric structure in which the ligands L are non-stoichiometrically substituted for the oxo or hydroxy groups and wherein the solid ligand-modified poly oxo-hydroxy metal ion material having one or more reproducible physico-chemical properties.

2. The method of treating hyperphosphatemia according to claim 1, wherein the carboxylic acid ligand is a linear dicarboxylic acid ligand.

3. The method of treating hyperphosphatemia according to claim 2, wherein the carboxylic acid ligand is represented by the formula HOOC—$R_1$—COOH, where $R_1$ is an optionally substituted alkyl, alkenyl or alkynyl group, or an ionised form thereof.

4. The method of treating hyperphosphatemia according to claim 3, wherein $R_1$ is a $C_{1-10}$ alkyl group, and more preferably is a $C_{2-6}$ alkyl group, wherein $R_1$ is optionally substituted with one or more hydroxyl group.

5. The method of treating hyperphosphatemia according to claim 1, wherein the carboxylic acid ligand is succinic acid, malic acid, adipic acid, glutaric acid or pimelic acid, or an ionised form thereof.

6. The method of treating hyperphosphatemia according to claim 1, wherein the material has a ferrihydrite structure as determined using electron diffraction.

7. The method of treating hyperphosphatemia according to claim 1, wherein the one or more reproducible physico-chemical properties comprise a dissolution profile and/or phosphate binding properties.

8. The method of treating hyperphosphatemia according to claim 7, wherein the phosphate binding properties comprise specificity for phosphate, affinity for phosphate and/or binding capacity for phosphate.

9. The method of treating hyperphosphatemia according to claim 7, wherein the phosphate binding capacity of 53.6 mg of the material is at least 50% of the 10 mM phosphate in a sample at a pH between 3 and 7, in a volume of 20 mL.

10. The method of treating hyperphosphatemia according to claim 1, wherein the material has demonstrable M-L bonding as determined using infrared spectroscopy.

11. The method of treatment according to claim 1, wherein M is $Fe^{3+}$ ions.

12. The method of treatment according to claim 1, wherein the composition further comprises a phosphate uptake inhibitor and/or a substance capable of ameliorating gastric side effects.

13. The method of treatment according to claim 12, wherein the phosphate uptake inhibitor and/or the substance capable of ameliorating gastric side effects is a further ligand incorporated into the solid ligand-modified poly oxo-hydroxy metal ion material, or is formulated in a composition with the solid ligand-modified poly oxo-hydroxy metal ion material.

14. The method of treatment according to claim 1, wherein the material is FeOH Ad100, FeOH Ad100 $SiO_2$, FeOH Glutaric 100, or FeOH Pimelic 100.

15. The method of treatment according to claim 1, wherein the patient having hyperphosphatemia has renal disease.

16. The method of treatment according to claim 15, wherein the renal disease is chronic renal disease, end stage renal disease, hyperphosphatemia arising from any level of renal insufficiency or acute renal failure.

17. The method of treatment according to claim 1, wherein the patient having hyperphosphatemia is undergoing haemodialysis.

18. The method of treatment according to claim 1, wherein the patient having hyperphosphatemia has elevated plasma phosphorus levels.

19. The method of treatment according to claim 1, wherein the complication or secondary condition is secondary hyperthyroidism, soft tissue calcification, osteodystrophy, hypercalcaemia, hyperparathyroidism reduction, cardiovascular morbidity or mortality, renal osteodystrophy and/or calciphylaxis.

20. The method of treatment according to claim 1, wherein the composition is formulated for oral or nasogastric administration.

21. A food-stuff or dialysis fluid comprising a phosphate binder that is a solid ligand-modified poly oxo-hydroxy metal ion material represented by the formula $(M_xL_y(OH)_n)$, wherein M represents one or more metal ions that comprise $Fe^{3+}$ ions, L represents one or more ligands that comprise a carboxylic acid ligand, or an ionised form thereof, and OH represents oxo or hydroxy groups and wherein the material has a polymeric structure in which the ligands L are non stoichiometrically substituted for the oxo or hydroxy groups and wherein the solid ligand-modified poly oxo-hydroxy metal ion material having one or more reproducible physico-chemical properties.

22. A method for removing phosphate from a medium, the method comprising (a) contacting a medium containing phosphate with a ferric iron composition, said composition being a solid ligand-modified poly oxo-hydroxy metal ion material represented by the formula $(M_xL_y(OH)_n)$, wherein M represents one or more metal ions that comprise $Fe^{3+}$, L represents one or more ligands that comprise a carboxylic acid ligand, or an ionised form thereof, and OH represents oxo or hydroxy groups and wherein the material has a polymeric structure in which the ligands L are non-stoichiometrically substituted for the oxo or hydroxy groups and wherein the solid ligand-modified poly oxo-hydroxy metal ion material having one or more reproducible physico-chemical properties said contacting occurring under conditions in which the phosphate is capable of binding to the ferric iron composition and (b) separating the bound phosphate from the composition.

23. The method of claim 22, wherein the medium is a solution or suspension.

24. The method of treatment according to claim 1, wherein said phosphate binder is administered to effect removal of phosphate from the gastrointestinal tract.

25. The method of claim 22, wherein said medium is selected from the group consisting of food-stuffs prior to consumption dialysis fluids, plasma, whole blood and a combination of plasma and whole blood.

26. The method of claim 25, wherein the medium is dialysis fluid which is contacted with said composition extracorporeally during haemodialysis.

27. A process for producing a phosphate binder, wherein the phosphate binder is a solid ligand-modified poly oxo-hydroxy metal ion material represented by the formula $(M_xL_y(OH)_n)$, wherein M represents one or more metal ions that comprise $Fe^{3+}$ ions, L represents one or more ligands that comprise a carboxylic acid ligand, or an ionised form thereof, and OH represents oxo or hydroxy groups and wherein the material has a polymeric structure in which the ligands L are non-stoichiometrically substituted for the oxo or hydroxy groups and wherein the solid ligand-modified poly oxo-hydroxy metal ion material having one or more reproducible physico-chemical properties, the process comprising:
  (a) mixing a solution comprising $Fe^{3+}$ and a carboxylic acid ligand, and optionally one or more further ligands or reaction components, in a reaction medium at a first pH(A) at which the components are soluble;
  (b) changing the pH(A) to a second pH(B) to cause a solid precipitate or a colloid of the ligand-modified poly oxo-hydroxy metal ion material to be formed;
  (c) separating, and optionally drying and/or formulating, the solid ligand-modified poly oxo-hydroxy metal ion material produced in step (b).

28. The process of claim 27, further comprising testing the phosphate binder in vitro or in vivo to determine at least one property of the phosphate binder.

29. The process of claim 28, wherein the at least one property is a dissolution profile and a phosphate binding property.

30. The process of claim 27, wherein the first pH(A) is less than 2.0 and the second pH(B) is between 3.0 and 12.0.

31. The process of claim 27, wherein the process is carried out room temperature (20-25° C.).

32. The process of claim 27, wherein in step (a), the solution contains 20 to 100 mM $Fe^{3+}$ and 50 to 250 mM adipic acid.

33. The process of claim 27, further comprising chemically or physically altering the final particle size of the ferric iron composition.

34. The process of claim 27, further comprising formulating the ferric iron composition.

35. The process of claim 27, wherein in step (a), the solution contains about 40 mM $Fe^{3+}$ and about 100 mM adipic acid.

* * * * *